(12) United States Patent
Bluth et al.

(10) Patent No.: US 6,692,436 B1
(45) Date of Patent: Feb. 17, 2004

(54) HEALTH CARE INFORMATION SYSTEM

(75) Inventors: Charles Bluth, Incline Village, NV (US); James Bluth, Verdi, NV (US)

(73) Assignee: Computerized Screening, Inc., Sparks, NV (US)

( * ) Notice: Subject to any disclaimer, the term of this patent is extended or adjusted under 35 U.S.C. 154(b) by 0 days.

(21) Appl. No.: 09/549,451

(22) Filed: Apr. 14, 2000

(51) Int. Cl.[7] .............................. A61B 5/00; G06F 19/00
(52) U.S. Cl. ........................ 600/300; 705/1; 128/904; 128/920; 600/301; 702/19
(58) Field of Search .................. 705/2–4, 10, 14; 600/300–301, 481–485; 128/903–904, 920–925; 700/200–209; 379/106.1–106.2; 482/8–9; 348/14–15; 235/375; 177/264; 702/127, 19; 708/131

(56) References Cited

U.S. PATENT DOCUMENTS

| | | | |
|---|---|---|---|
| 4,677,983 A | | 7/1987 | Yamaguchi et al. |
| 4,998,534 A | | 3/1991 | Claxton, III et al. |
| 5,054,495 A | | 10/1991 | Uemura et al. |
| 5,140,991 A | | 8/1992 | Niwa |
| D371,844 S | | 7/1996 | Sadritabrizi et al. |
| 5,533,511 A | | 7/1996 | Kaspari et al. |
| 5,647,369 A | | 7/1997 | Petrucelli et al. |
| 5,704,362 A | | 1/1998 | Hersh et al. |
| 5,867,821 A | * | 2/1999 | Ballantyne et al. ............ 705/2 |
| 5,954,640 A | * | 9/1999 | Szabo ........................ 600/300 |
| 5,961,451 A | * | 10/1999 | Reber et al. ................. 600/322 |
| 6,046,761 A | * | 4/2000 | Echerer ....................... 348/15 |
| 6,050,924 A | * | 4/2000 | Shea ............................. 482/8 |
| 6,080,106 A | * | 6/2000 | Lloyd et al. ................ 600/300 |
| 6,101,478 A | * | 8/2000 | Brown ....................... 600/300 |
| 6,206,829 B1 | * | 3/2001 | Iliff et al. ................... 600/300 |
| 6,290,646 B1 | * | 9/2001 | Cosentino et al. .......... 600/300 |
| 6,454,705 B1 | * | 9/2002 | Cosentino et al. .......... 600/300 |

FOREIGN PATENT DOCUMENTS

| | | |
|---|---|---|
| EP | 0 422 512 | 4/1991 |
| WO | WO 95/18564 | 7/1995 |

* cited by examiner

*Primary Examiner*—Max F. Hindenburg
*Assistant Examiner*—Michael Astorino
(74) *Attorney, Agent, or Firm*—Parsons Hsue & de Runtz LLP

(57) ABSTRACT

A health kiosk provides blood pressure testing, a health and fitness evaluation, and a medication encyclopedia. The health kiosk typically interfaces to a computer or server, such as a pharmacy computer or a remote server which compares pharmaceuticals selected by a user to information in the medication encyclopedia to determine compatibility for prescription medications and over-the-counter medications. In some systems, the kiosk also supplies one item or more of an extended health information, a weight scale constructed into the seat of the kiosk, a directory of health care service and product providers, an a directory of community health, support, and service groups.

57 Claims, 21 Drawing Sheets

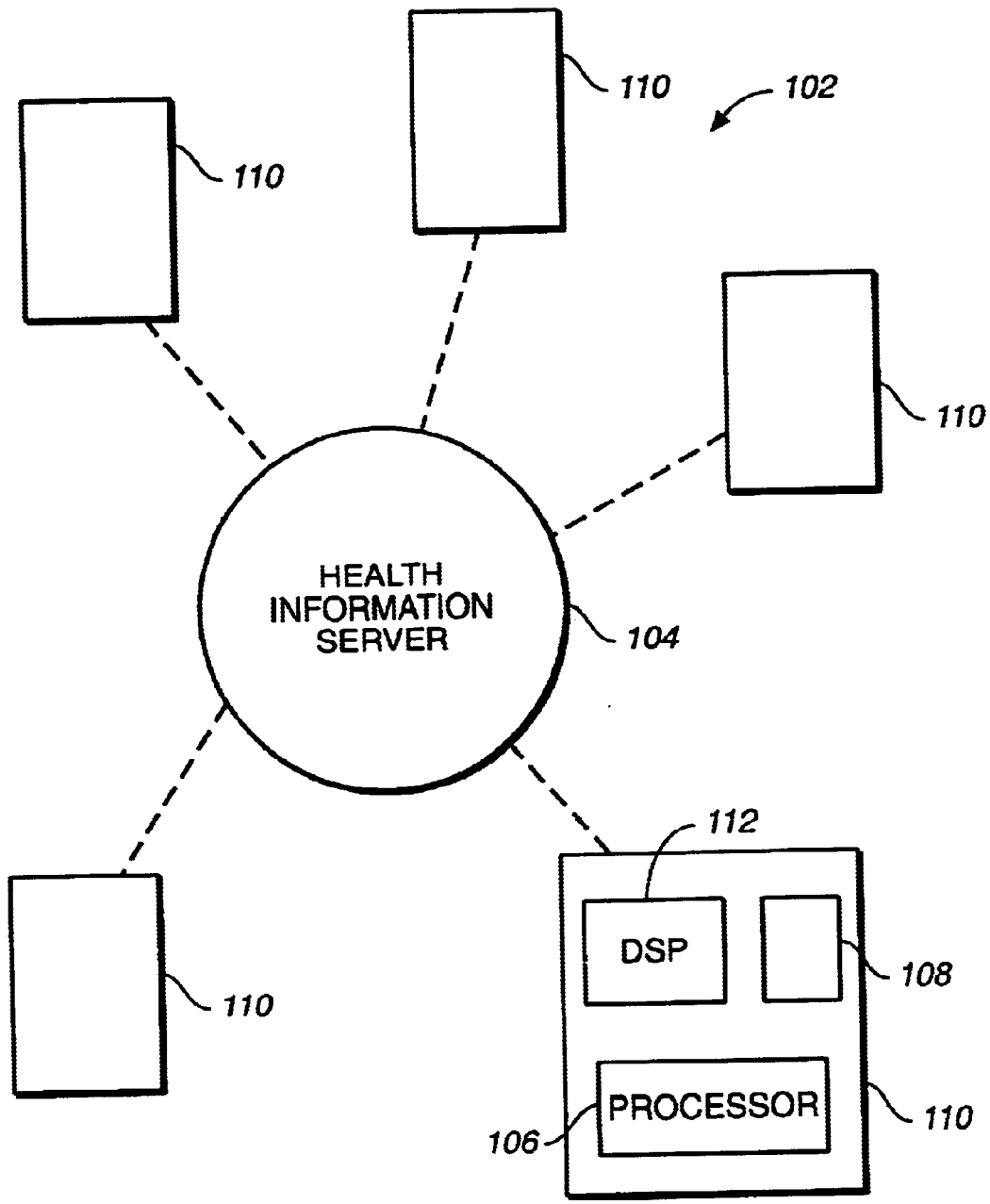
FIG._1

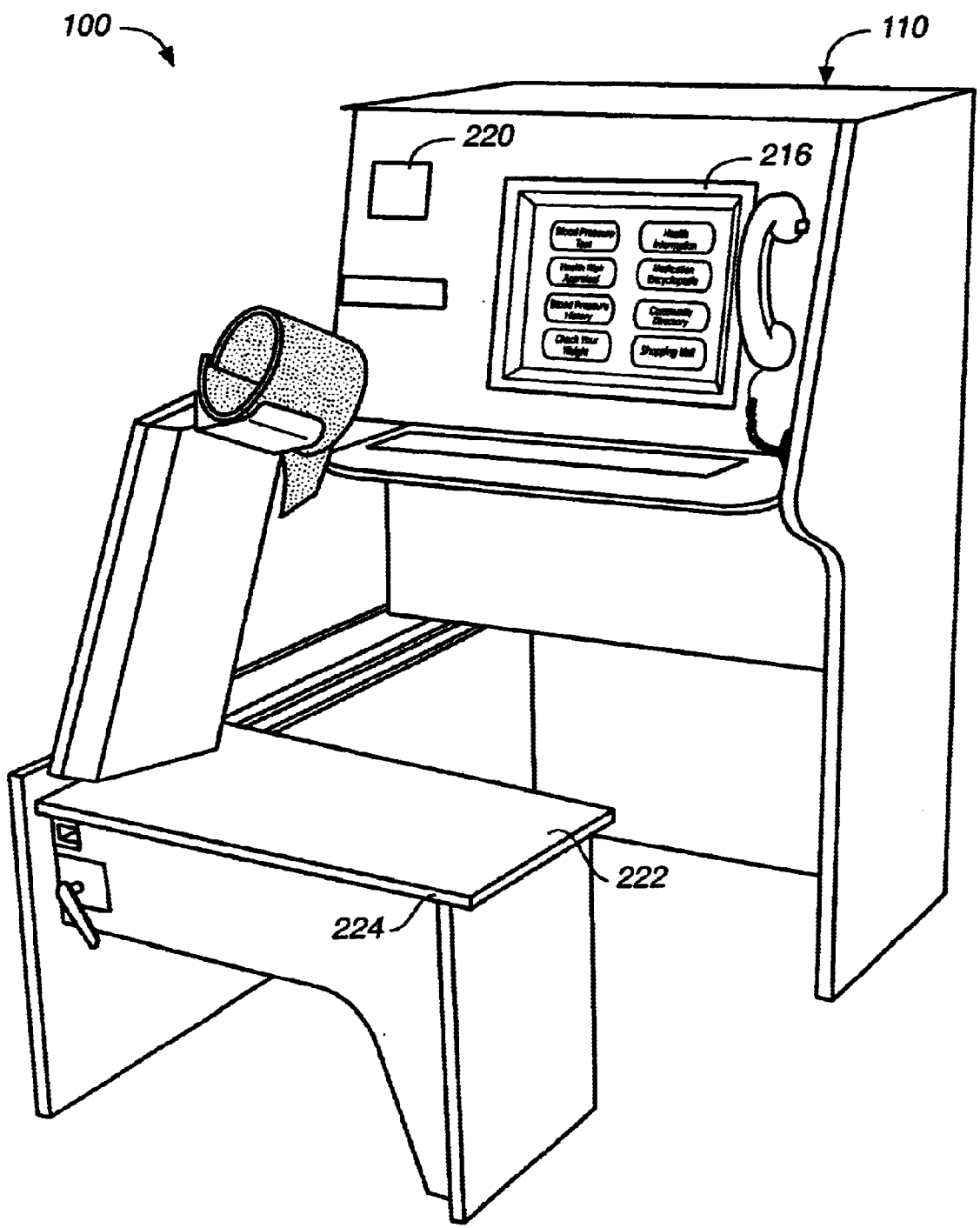
FIG._2

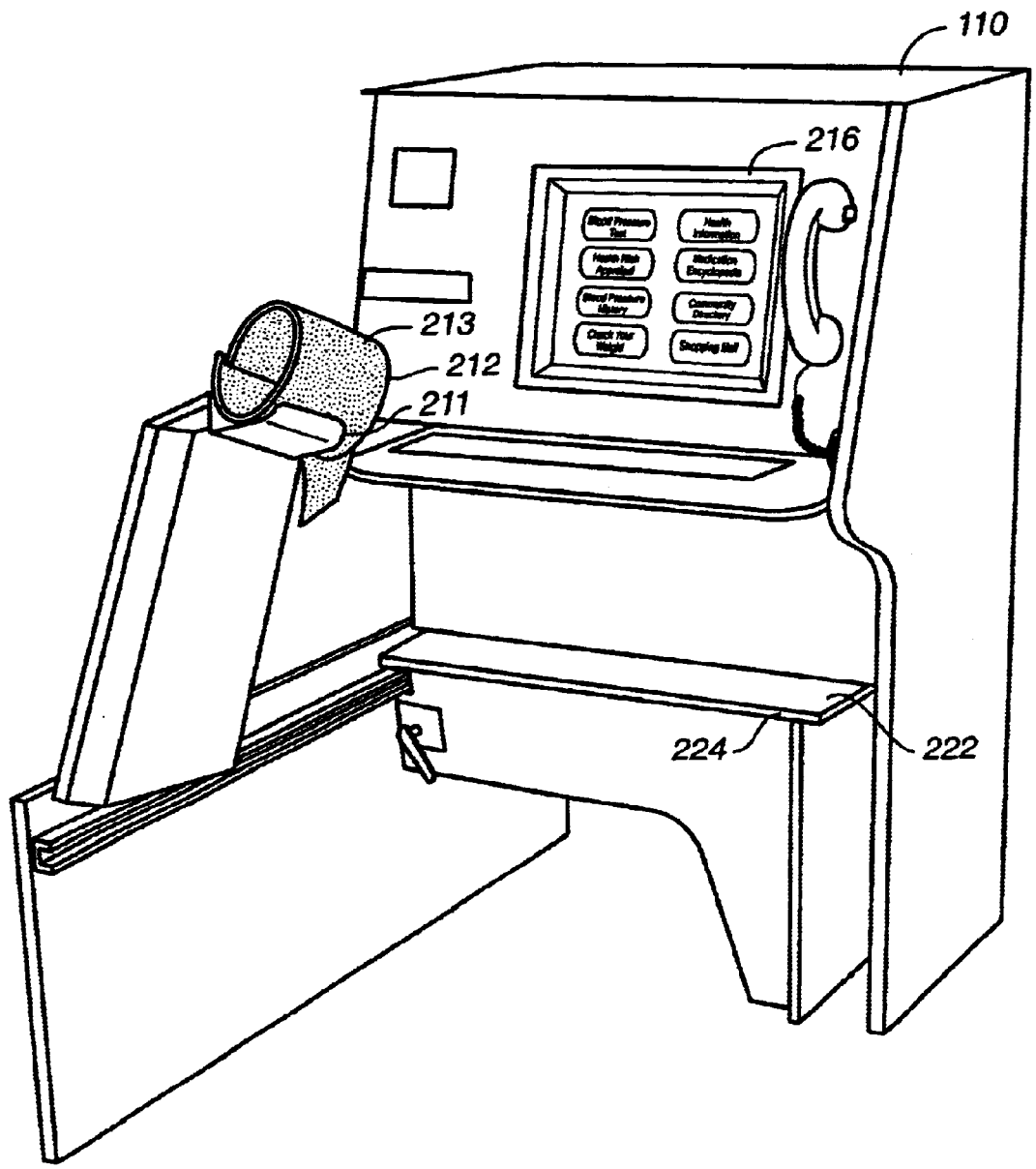
FIG._3

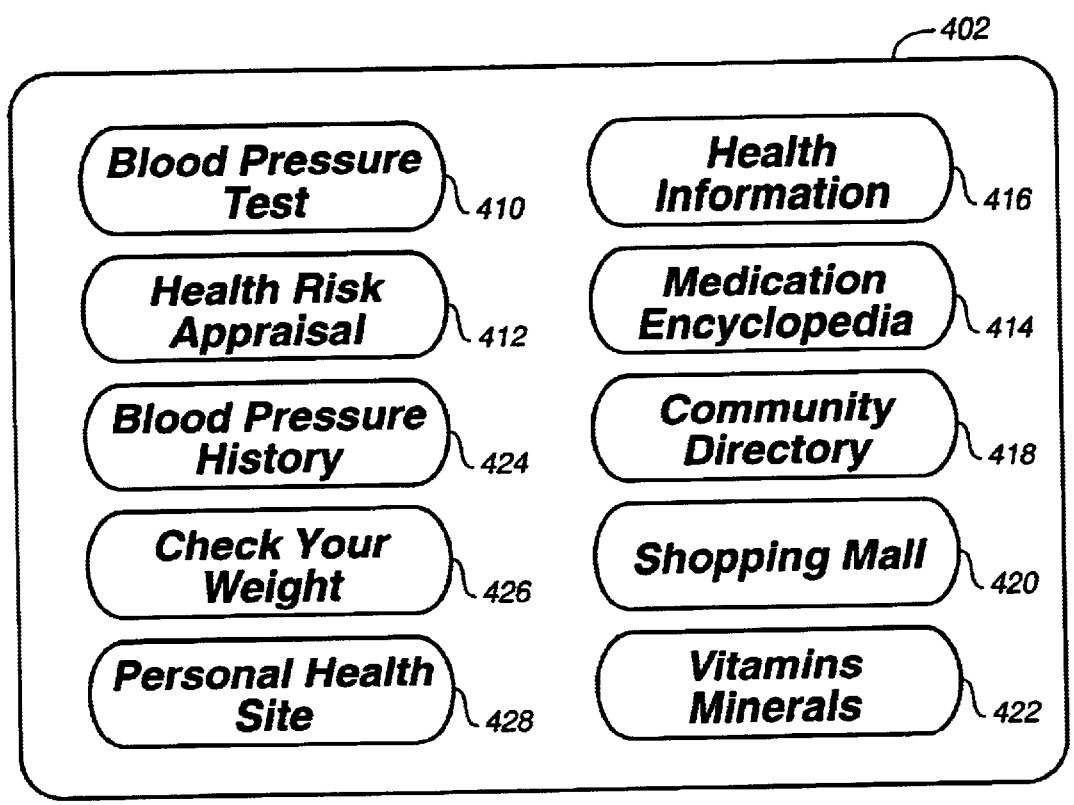
FIG._4

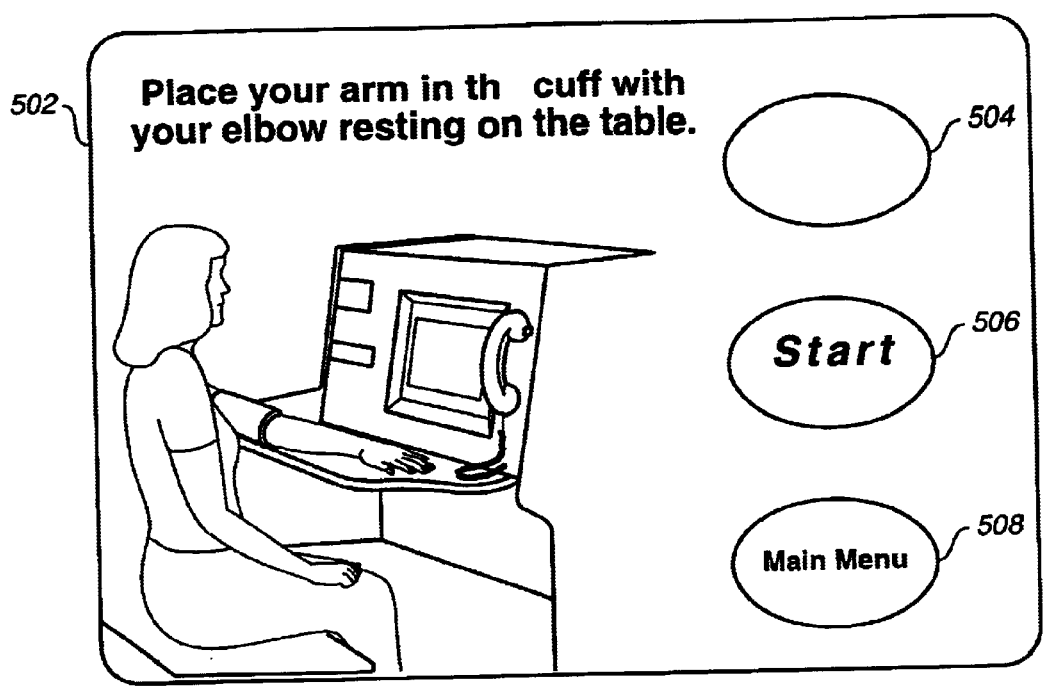
FIG._5A
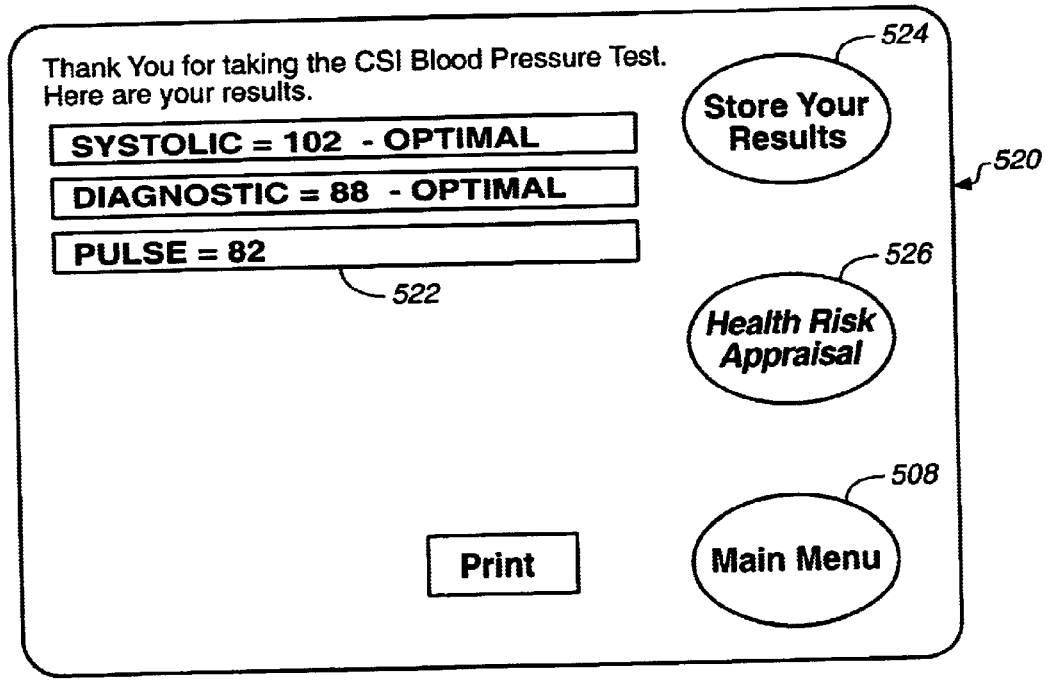
FIG._5B

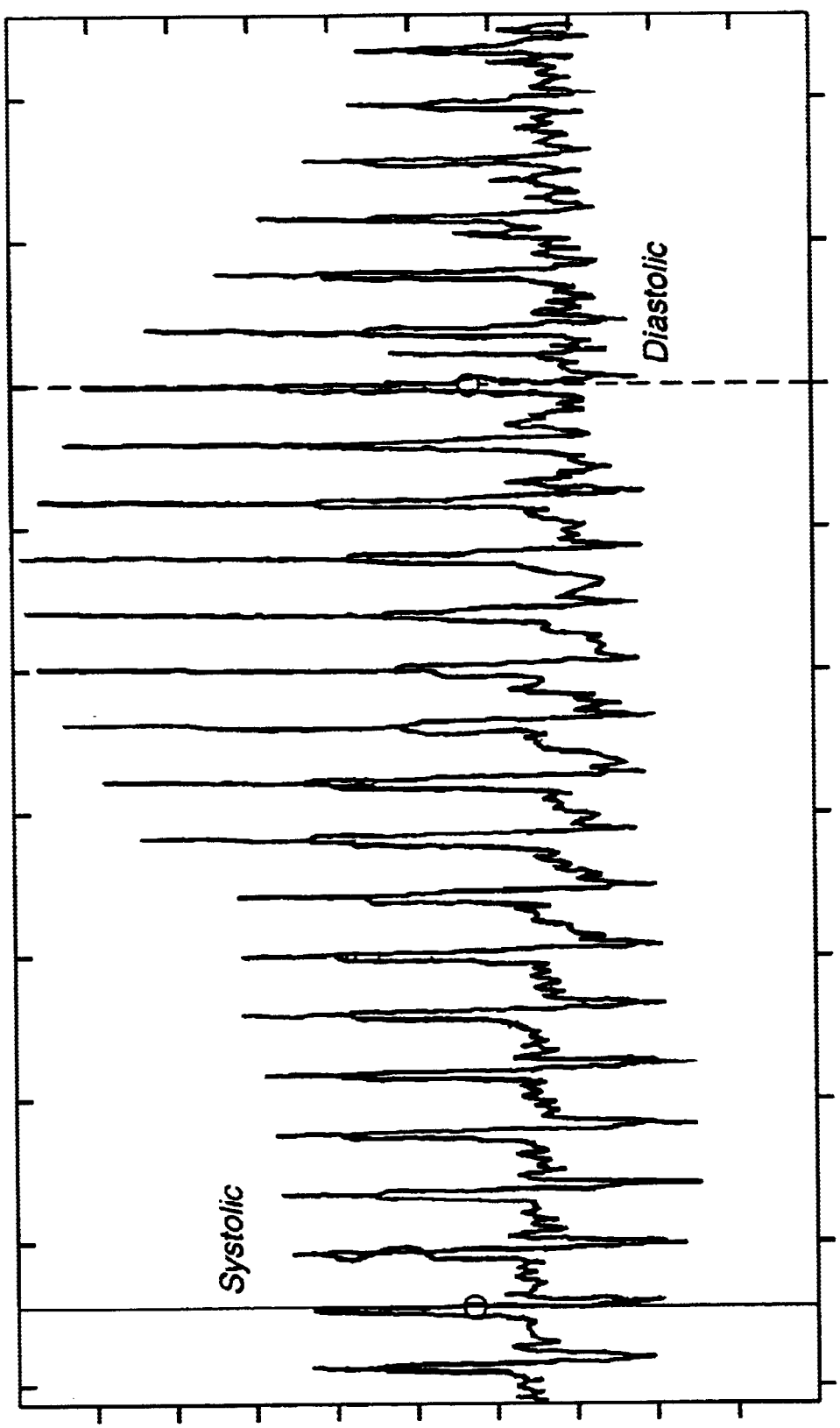
FIG._6A

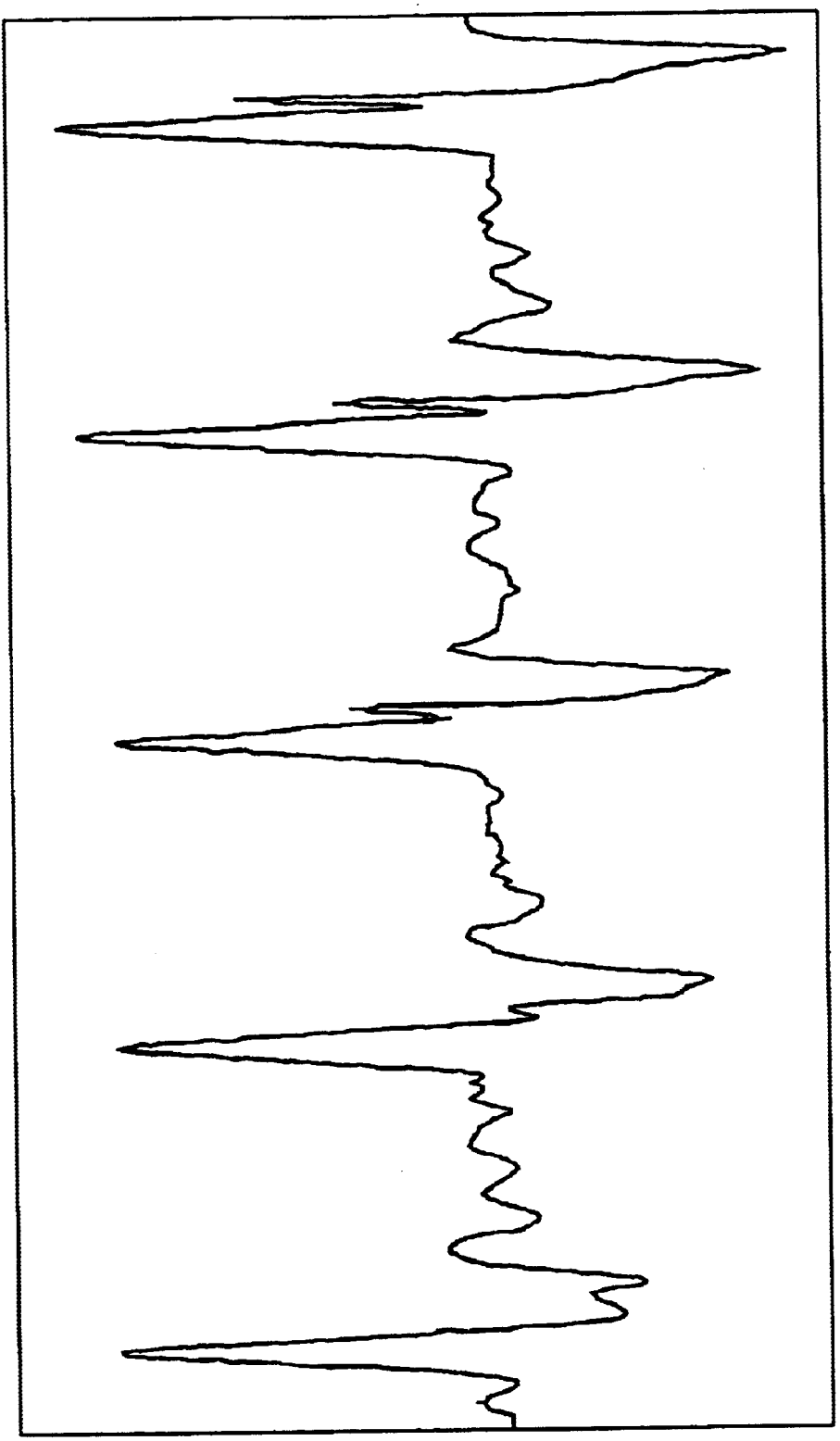
FIG._6B

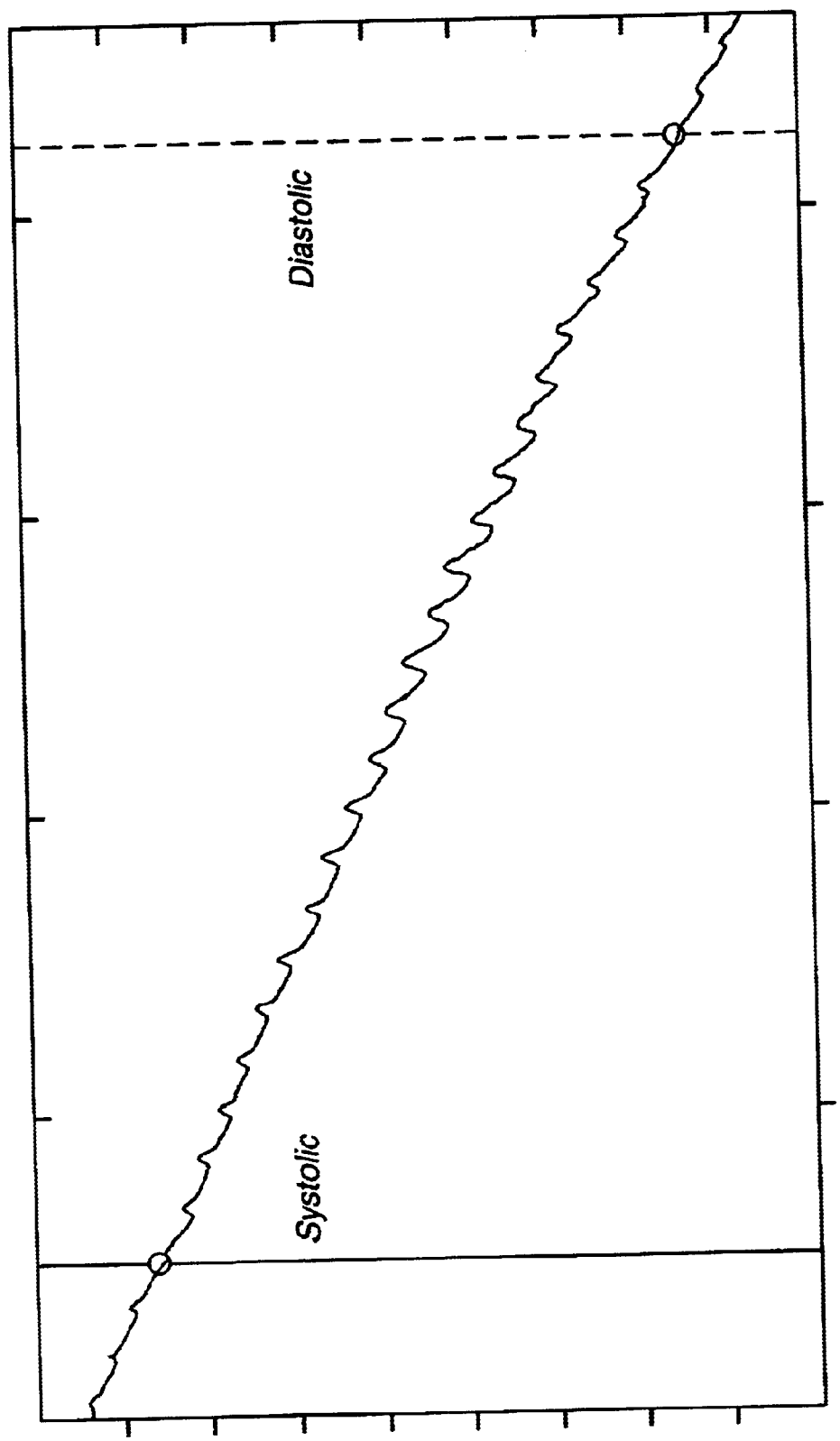
FIG._6C

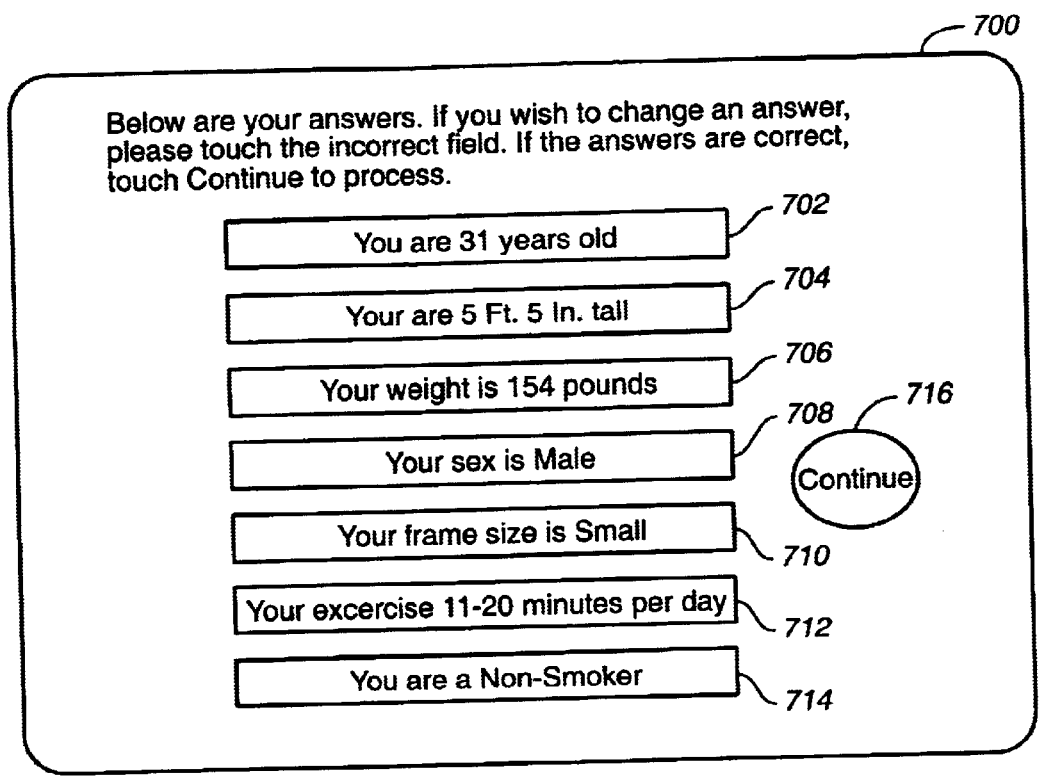
FIG._7A
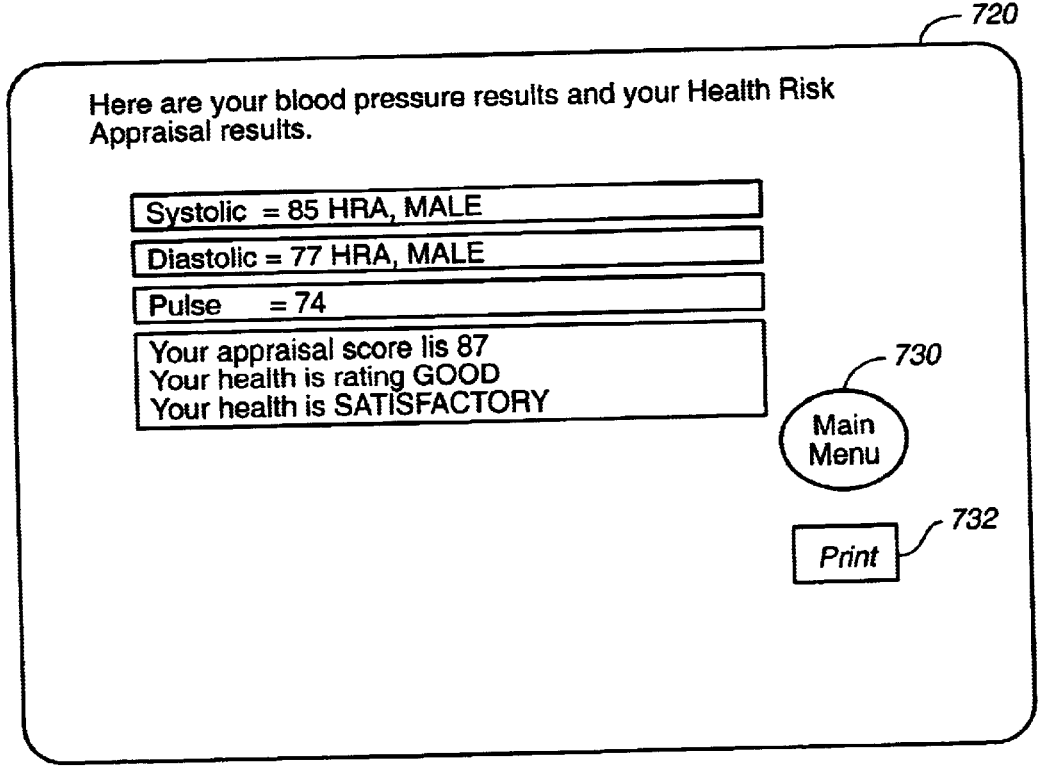
FIG._7B

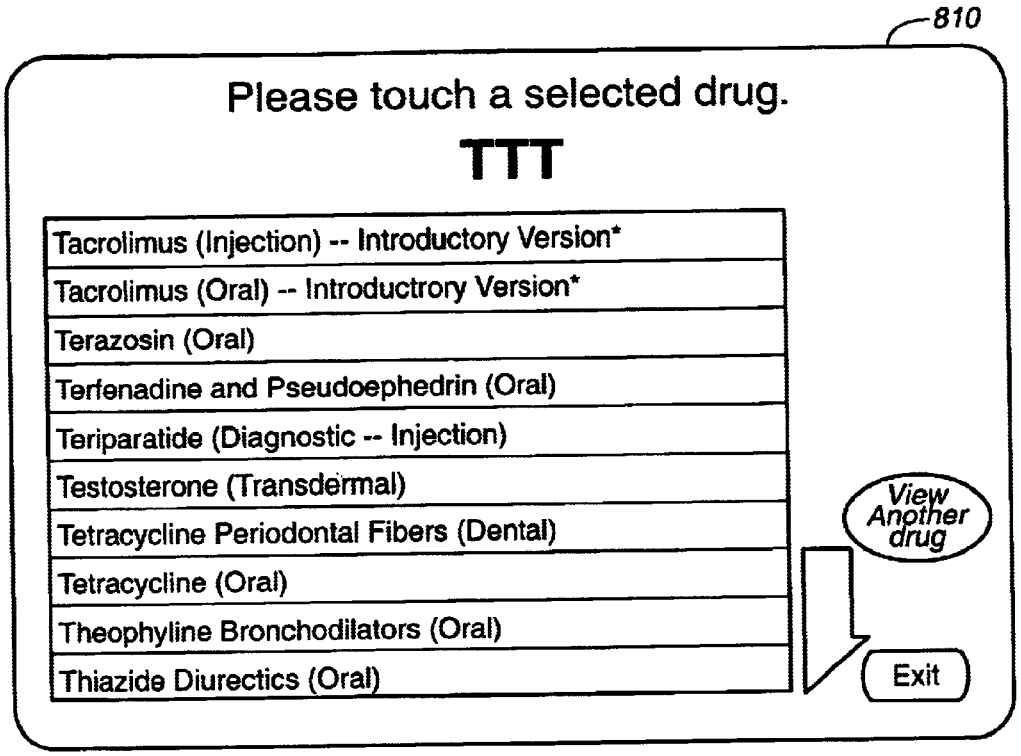
FIG._8A
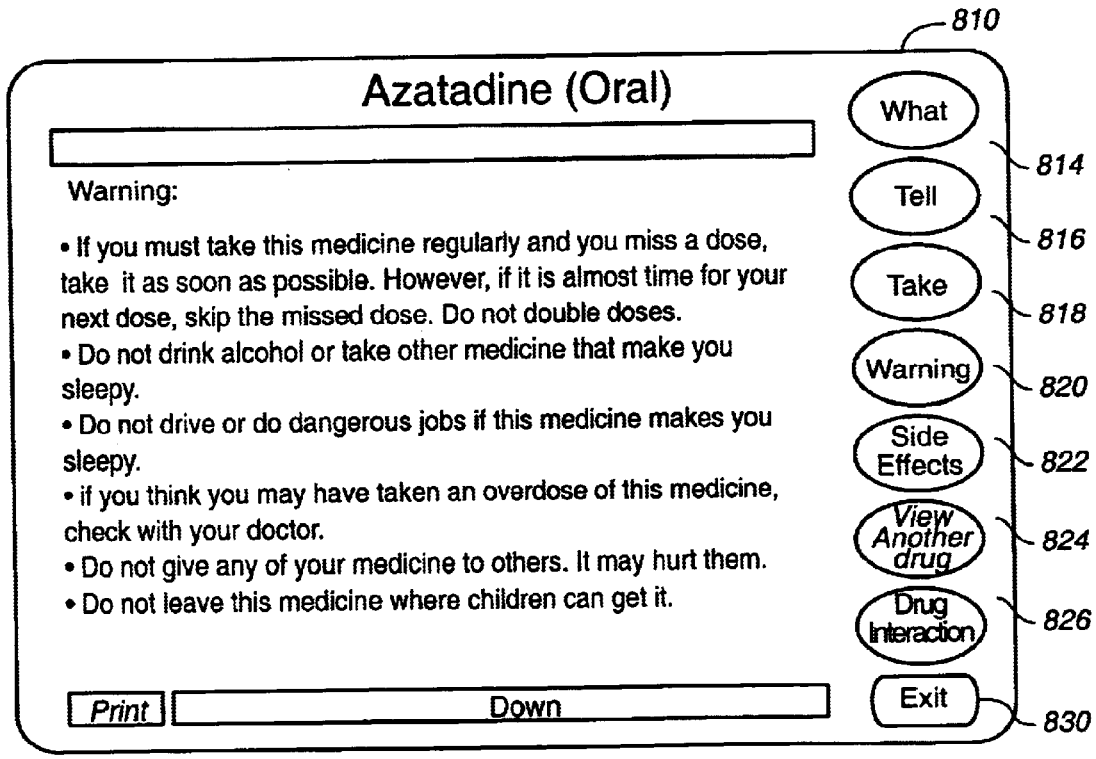
FIG._8B

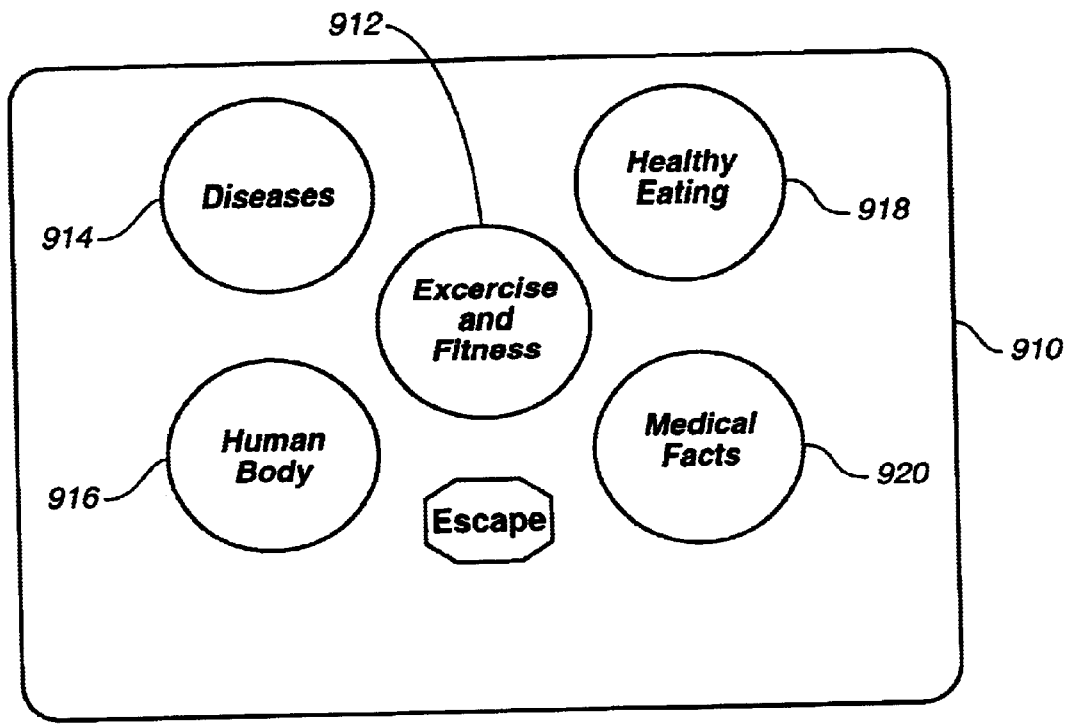
FIG._9A
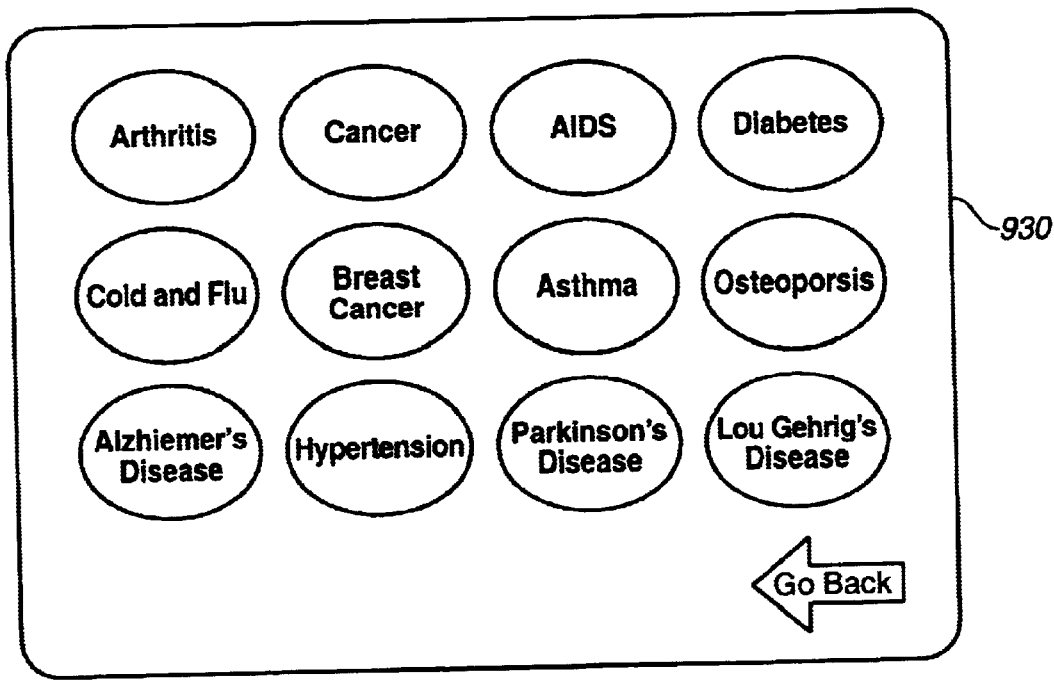
FIG._9B

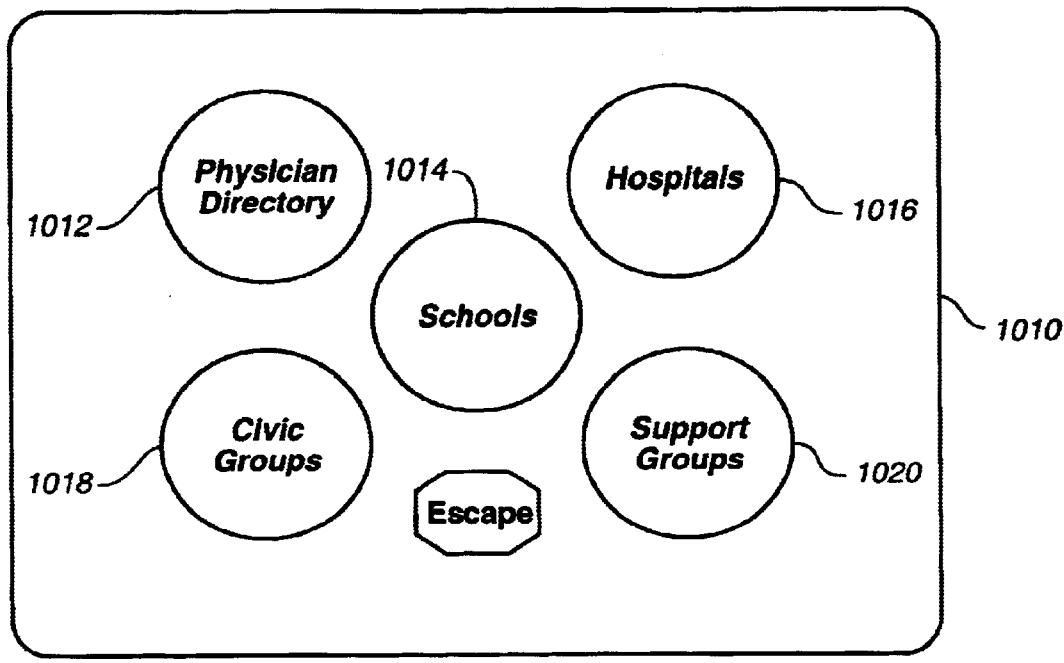
FIG._10A
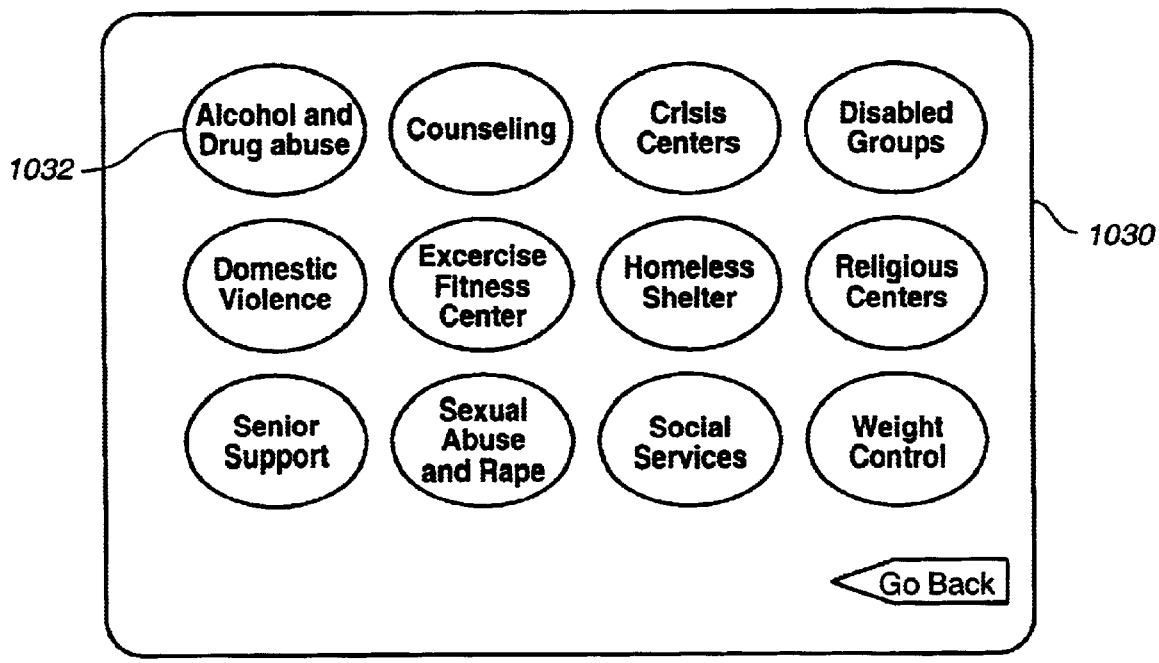
FIG._10B

| | | |
|---|---|---|
| A New Choice Counseling DUI Program | 1210 S. Sierra | (702) 322-4500 |
| AAA Fresh Start | 1016 N. Rock Blvd. | (702) 358-1011 |
| ACES DUI School | 975 Ryland | (702) 329-5737 |
| Alcoholics Anonymous | 418 S. Rock Blvd. | (702) 355-1151 |
| Alpine Counseling Associates | 515 S. Arlington | (702) 786-7343 |
| Associated Counseling | 676 Fairview Dr. | (702) 887-0677 |
| Basic Recovery Associates Inc. | 1095 S. Virginia | (702) 329-4771 |
| Betty Ford Center | 39000 Bob Hope Dr. | (800) 854-9211 |
| Cage Counseling | P. O. Box 50147 | (702) 322-1697 |
| Capital City Alano Club | 1803 N. Carson | (702) 884-1697 |
| Carson Detoxification Center | 120 N. Harbin Ave. | (702) 885-2727 |
| Centers for Behavioral Health | 160 Hubbard Way | (702) 829-4472 |
| Choices Unlimited | 200 Court St. | (702) 324-5022 |
| Community Counseling Center | 625 Fairview Dr. | (702) 882-3945 |
| Evergreen Evaluation Education Center | 955 S. Virginia | (702) 324-0600 |

Down    < Go Back

FIG._10C

Alcoholics Anonymous
Central Office/24 hour hotline
355-1151
Located at 418 S. Rock Blvd.
Sparks
Office hours are 9:00 a.m. to 5:00 p.m.
Monday - Friday
The main office provides information for all local Reno/Sparks and eastern Nevada AA meetings
There is no fee or appointments necessary. There are a total of 210 meetings in each area. Locations of these meetings are provided in the central office.

Touch here to call Alcoholics Anonymous dir ctly    < Go Back

FIG._10D

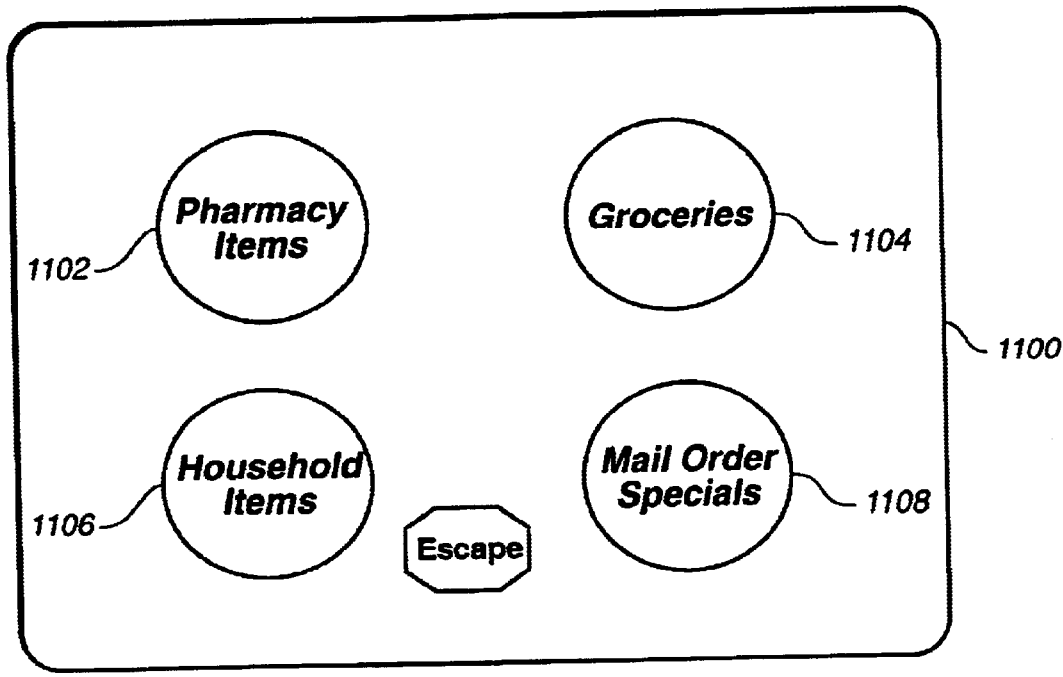
FIG._11A
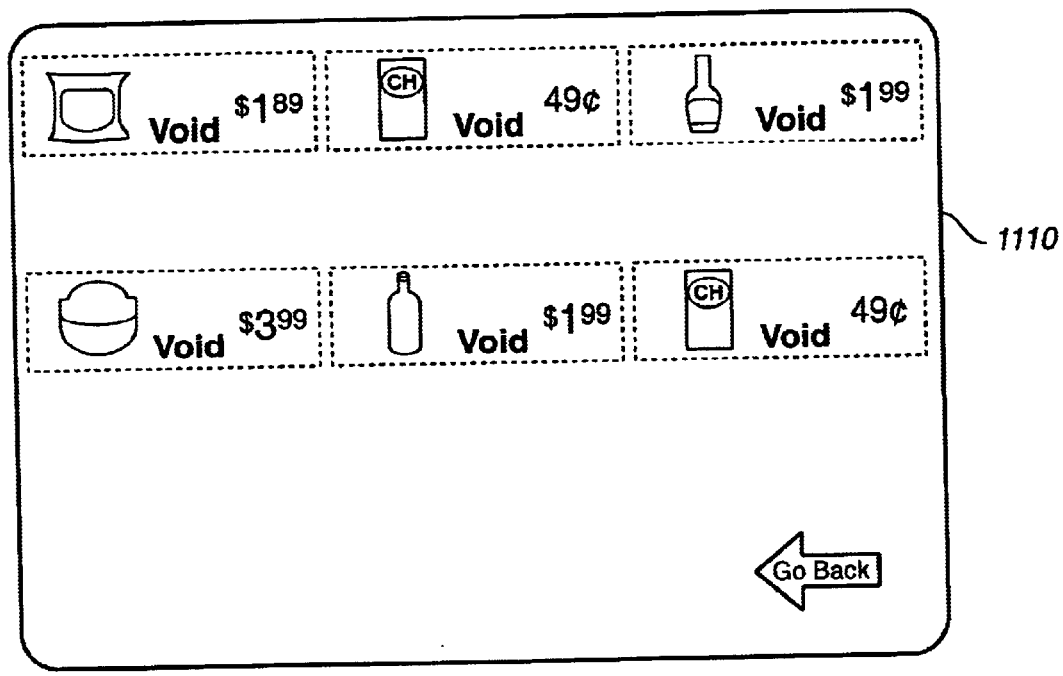
FIG._11B

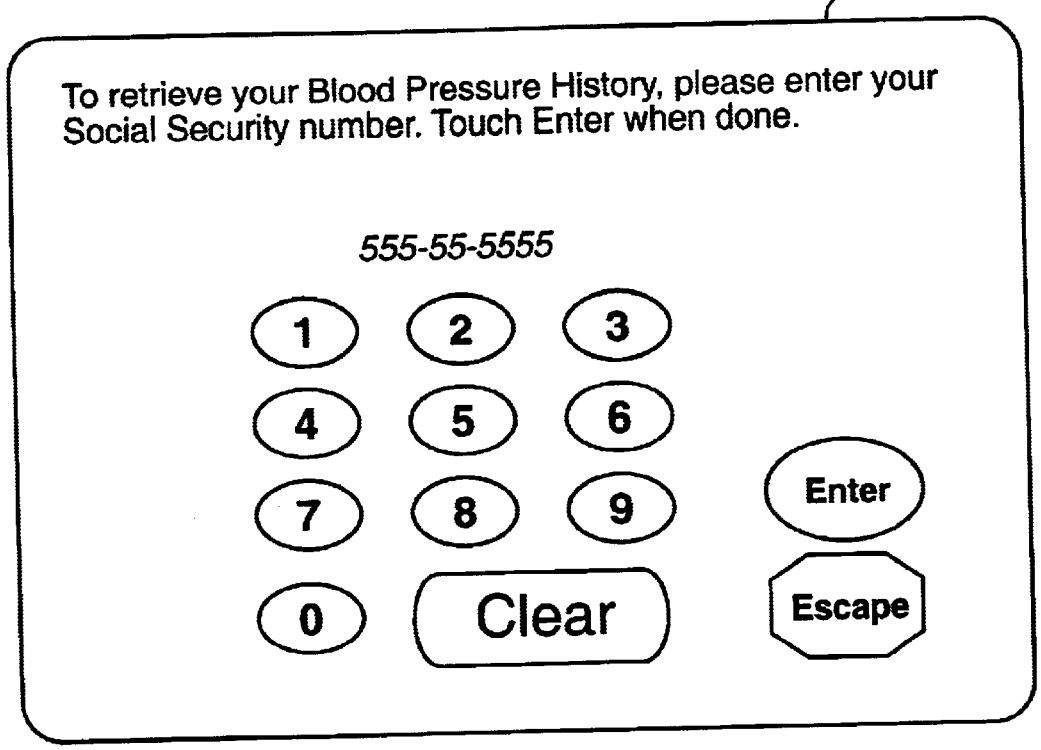
FIG._12A
FIG._12B

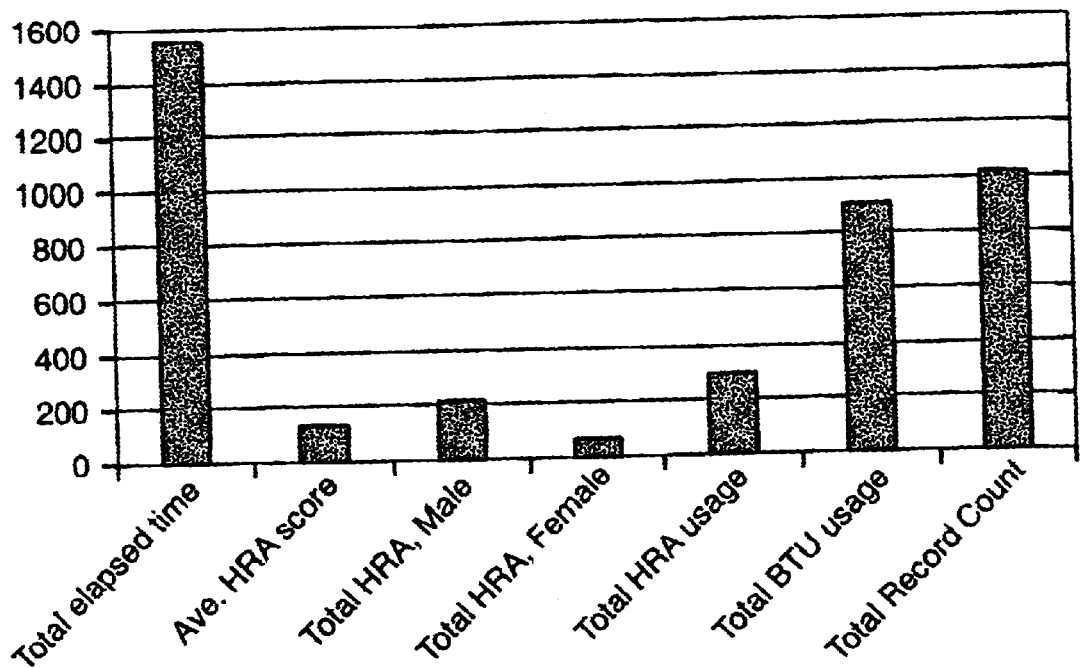
FIG._13A
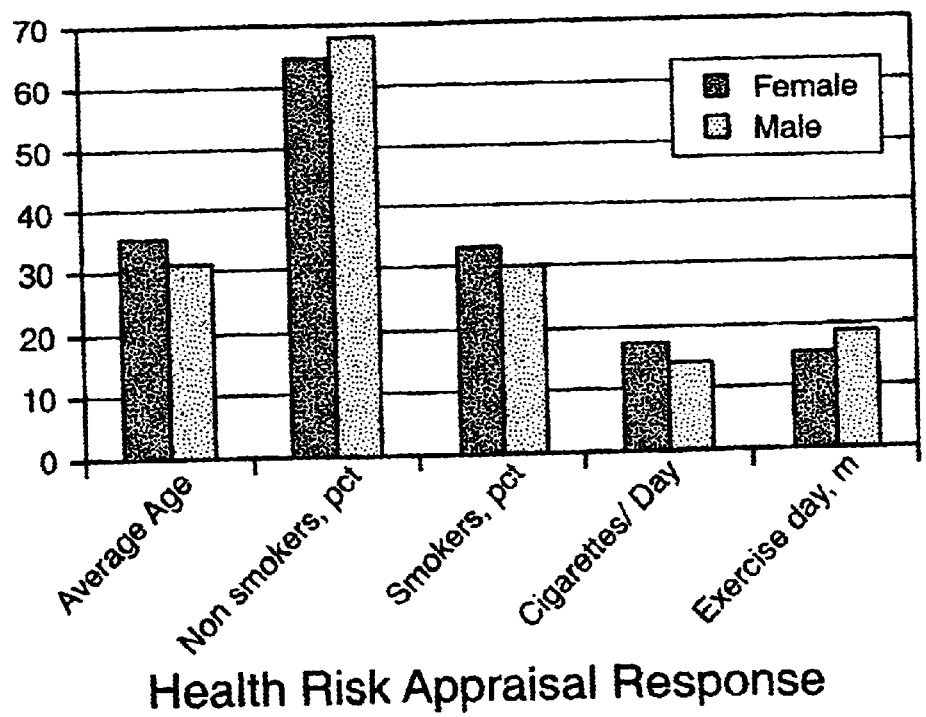
Health Risk Appraisal Response
FIG._13B

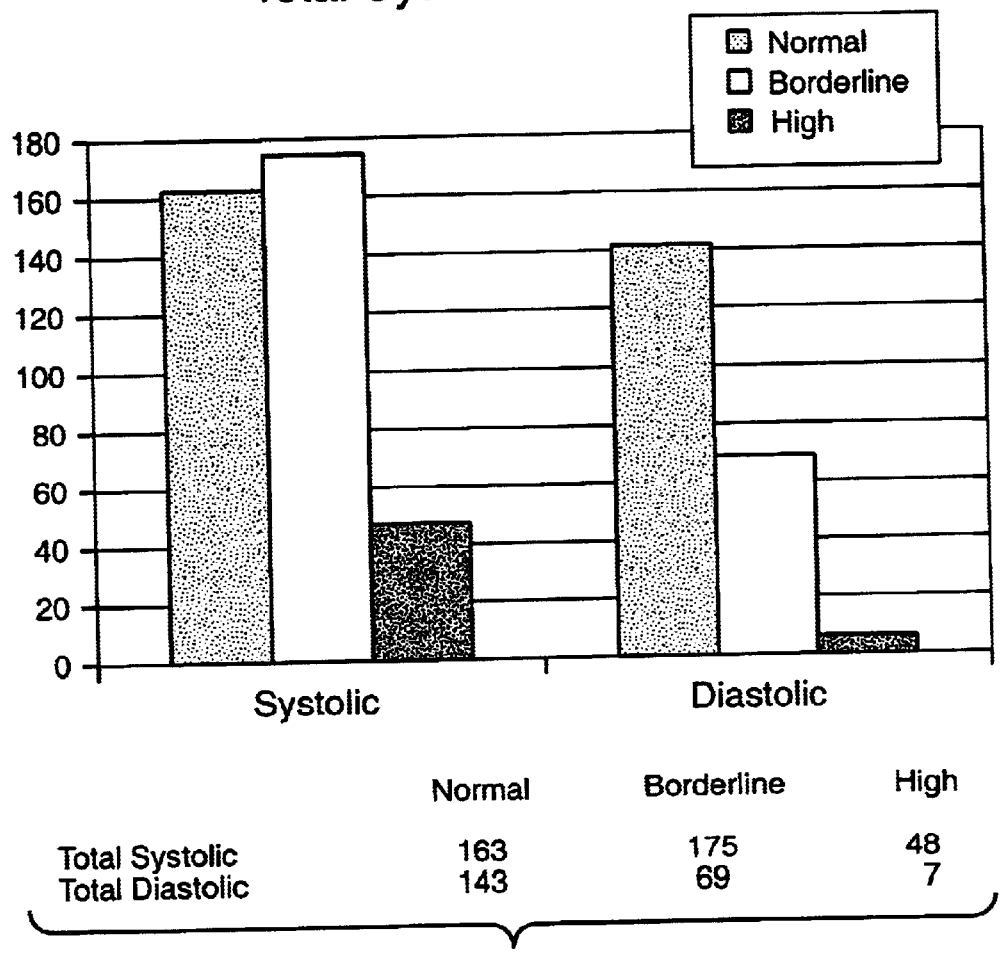
FIG._13C

| Rec | Yr | Mo | Dy | Hr | Mn | Sy | Di | Pu | BPx | Sx | Ag | Ht | Wt | Ex | Sk | Fs | BPT | HRA | BB3 | BB4 | ET |
|---|---|---|---|---|---|---|---|---|---|---|---|---|---|---|---|---|---|---|---|---|---|
| 1 | 96 | 11 | 11 | 20 | 29 | 107 | 69 | 57 | 1 | 0 | 0 | 0 | 0 | 0 | 0 | 0 | 1 | 0 | 0 | 0 | 1:20 |
| 2 | 96 | 11 | 22 | 22 | 43 | 97 | 66 | 75 | 1 | 0 | 0 | 0 | 0 | 0 | 0 | 0 | 1 | 0 | 0 | 0 | 1:10 |
| 3 | 96 | 11 | 22 | 20 | 22 | 112 | 66 | 76 | 1 | 0 | 0 | 0 | 0 | 0 | 0 | 1 | 1 | 0 | 0 | 0 | 0:59 |
| 4 | 96 | 11 | 5 | 20 | 21 | 106 | 66 | 82 | 1 | 1 | 22 | 68 | 135 | 2 | 1 | 0 | 0 | 0 | 0 | 0 | 1:47 |
| 5 | 96 | 11 | 5 | 20 | 29 | 119 | 67 | 79 | 1 | 0 | 0 | 0 | 0 | 0 | 0 | 0 | 1 | 0 | 0 | 0 | 0:52 |
| 6 | 96 | 11 | 5 | 20 | 25 | 118 | 66 | 83 | 1 | 0 | 0 | 0 | 0 | 0 | 0 | 0 | 1 | 0 | 0 | 0 | 0:54 |
| 7 | 96 | 11 | 5 | 20 | 23 | 118 | 64 | 92 | 1 | 0 | 0 | 0 | 0 | 0 | 0 | 0 | 1 | 0 | 0 | 0 | 0:53 |
| 8 | 96 | 11 | 20 | 1 | 16 | 108 | 68 | 72 | 1 | 0 | 0 | 0 | 0 | 0 | 0 | 0 | 1 | 0 | 0 | 0 | 1:26 |
| 9 | 96 | 11 | 24 | 17 | 59 | 117 | 69 | 86 | 1 | 0 | 0 | 0 | 0 | 0 | 0 | 0 | 0 | 0 | 0 | 0 | 1:15 |
| 10 | 96 | 11 | 26 | 18 | 39 | 111 | 77 | 83 | 1 | 0 | 0 | 0 | 0 | 0 | 0 | 0 | 1 | 0 | 0 | 0 | 1:32 |
| 11 | 96 | 12 | 3 | 16 | 45 | 104 | 69 | 64 | 1 | 0 | 0 | 0 | 0 | 0 | 0 | 0 | 0 | 0 | 0 | 0 | 1:15 |
| 12 | 96 | 11 | 24 | 13 | 43 | 114 | 72 | 66 | 1 | 1 | 48 | 72 | 180 | 3 | 1 | 0 | 1 | 0 | 0 | 0 | 3:03 |
| 13 | 96 | 11 | 18 | 18 | 7 | 113 | 69 | 80 | 1 | 0 | 0 | 0 | 0 | 0 | 0 | 0 | 1 | 0 | 0 | 0 | 1:17 |
| 14 | 96 | 12 | 4 | 0 | 26 | 111 | 69 | 81 | 1 | 0 | 0 | 0 | 0 | 0 | 0 | 0 | 1 | 0 | 0 | 0 | 1:19 |
| 15 | 96 | 12 | 2 | 1 | 50 | 103 | 66 | 89 | 1 | 0 | 0 | 0 | 0 | 0 | 0 | 0 | 0 | 0 | 0 | 0 | 1:36 |
| 16 | 96 | 11 | 25 | 2 | 49 | 111 | 71 | 71 | 1 | 0 | 0 | 0 | 0 | 0 | 0 | 0 | 1 | 0 | 0 | 0 | 1:34 |
| 17 | 96 | 11 | 20 | 16 | 59 | 111 | 67 | 74 | 1 | 0 | 0 | 0 | 0 | 0 | 0 | 0 | 1 | 0 | 0 | 0 | 1:32 |
| 18 | 96 | 12 | 1 | 2 | 10 | 118 | 77 | 57 | 1 | 0 | 0 | 0 | 0 | 0 | 0 | 0 | 0 | 0 | 0 | 0 | 0:59 |
| 19 | 96 | 11 | 17 | 2 | 4 | 116 | 72 | 83 | 1 | 0 | 0 | 0 | 0 | 0 | 0 | 0 | 1 | 0 | 0 | 0 | 1:01 |
| 20 | 96 | 11 | 16 | 20 | 47 | 111 | 73 | 74 | 1 | 1 | 30 | 72 | 216 | 3 | 1 | 3 | 1 | 0 | 0 | 0 | 2:03 |
| 21 | 96 | 11 | 20 | 13 | 21 | 109 | 69 | 81 | 1 | 1 | 30 | 72 | 215 | 3 | 1 | 3 | 1 | 0 | 0 | 0 | 1:59 |
| 22 | 96 | 12 | 4 | 8 | 25 | 93 | 72 | 68 | 1 | 0 | 0 | 0 | 0 | 0 | 0 | 0 | 0 | 0 | 0 | 0 | 1:18 |
| 23 | 96 | 12 | 2 | 2 | 9 | 116 | 72 | 77 | 1 | 0 | 0 | 0 | 0 | 0 | 0 | 0 | 1 | 0 | 0 | 0 | 1:01 |
| 24 | 96 | 11 | 14 | 14 | 26 | 84 | 67 | 0 | 1 | 0 | 0 | 0 | 0 | 0 | 0 | 0 | 0 | 0 | 0 | 0 | 0:59 |
| 25 | 96 | 11 | 21 | 15 | 51 | 119 | 69 | 63 | 1 | 1 | 30 | 72 | 215 | 3 | 1 | 3 | 1 | 0 | 0 | 0 | 2:23 |
| 26 | 96 | 11 | 13 | 8 | 1 | 104 | 67 | 79 | 1 | 1 | 30 | 72 | 216 | 4 | 1 | 3 | 1 | 0 | 0 | 0 | 2:10 |
| 27 | 96 | 11 | 28 | 1 | 12 | 115 | 72 | 69 | 1 | 1 | 30 | 72 | 215 | 3 | 1 | 3 | 1 | 0 | 0 | 0 | 2:00 |
| 28 | 96 | 11 | 18 | 17 | 44 | 108 | 69 | 78 | 1 | 0 | 0 | 0 | 0 | 0 | 0 | 0 | 1 | 0 | 0 | 0 | 0:57 |
| 29 | 96 | 11 | 30 | 22 | 55 | 104 | 69 | 87 | 1 | 0 | 0 | 0 | 0 | 0 | 0 | 0 | 0 | 0 | 0 | 0 | 1:28 |
| 30 | 96 | 11 | 18 | 9 | 9 | 119 | 65 | 81 | 1 | 0 | 0 | 0 | 0 | 0 | 0 | 0 | 1 | 1 | 1 | 1 | 1:20 |
| 31 | 96 | 11 | 25 | 11 | 22 | 119 | 66 | 66 | 1 | 1 | 23 | 0 | 167 | 3 | 1 | 2 | 0 | 0 | 0 | 0 | 2:21 |
| 32 | 96 | 11 | 22 | 1 | 13 | 86 | 69 | 0 | 1 | 0 | 0 | 0 | 0 | 0 | 0 | 0 | 1 | 0 | 0 | 0 | 1:01 |
| 33 | 96 | 11 | 22 | 18 | 9 | 101 | 66 | 78 | 1 | 0 | 0 | 0 | 0 | 0 | 0 | 0 | 1 | 0 | 0 | 0 | 1:19 |

FIG._14

BP RESULTS ← 1502

YOUR BLOOD PRESSURE TEST HAS BEEN COMPLETED. HERE ARE THE RESULTS.

SYSTOLIC = 112 - OPTIMAL
DIASTOLIC = 71 - OPTIMAL
PULSE = 65 -

05-10-1997          14:16:54

Thank you for visiting the CSI6000

HRA RESULTS ← 1504

HERE ARE YOUR HEALTH RISK APPRAISAL RESULTS.

YOUR SCORE IS: 95

RATE AS: EXCELLENT

YOUR HEALTH RISK IS: VERY LOW 05-10-1997          14:17:36

Thank you for visiting the CSI6000

BLOOD PRESSURE HISTORY FOR ← 1506
555-55-5555

| SYS | DIA | PULSE | TIME | DATE |
|---|---|---|---|---|
| 112 | 71 | 65 | 14:16 | 05-10-97 |
| 110 | 86 | 90 | 13:04 | 05-10-97 |
| 115 | 66 | 64 | 12:34 | 05-10-97 |
| 118 | 79 | 66 | 15:49 | 04-02-97 |
| 130 | 69 | 66 | 14:37 | 04-01-97 |
| 152 | 110 | 93 | 08:43 | 04-01-97 |
| 144 | 96 | 80 | 14:54 | 03-28-97 |
| 163 | 78 | 80 | 10:27 | 03-28-97 |

05-10-1997          14:18:05

Thank you for visiting the CSI6000

*(COUPON Xpress borders on left and right)*

FIG. 15

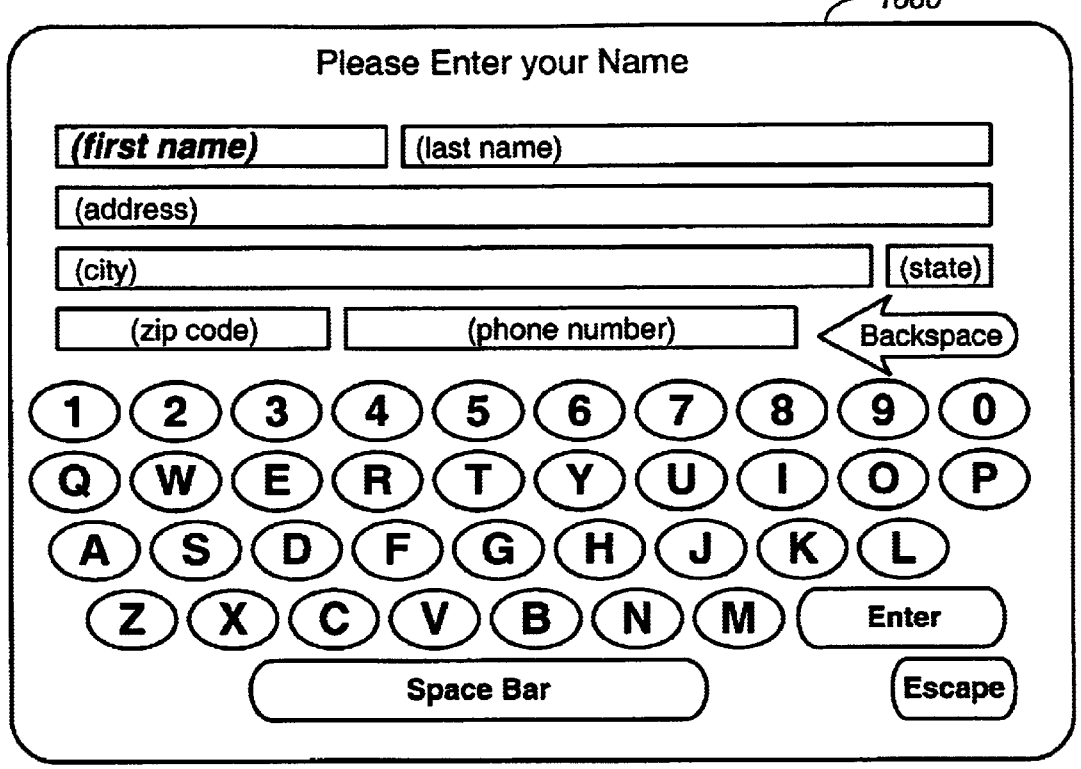
FIG._16
FIG._17

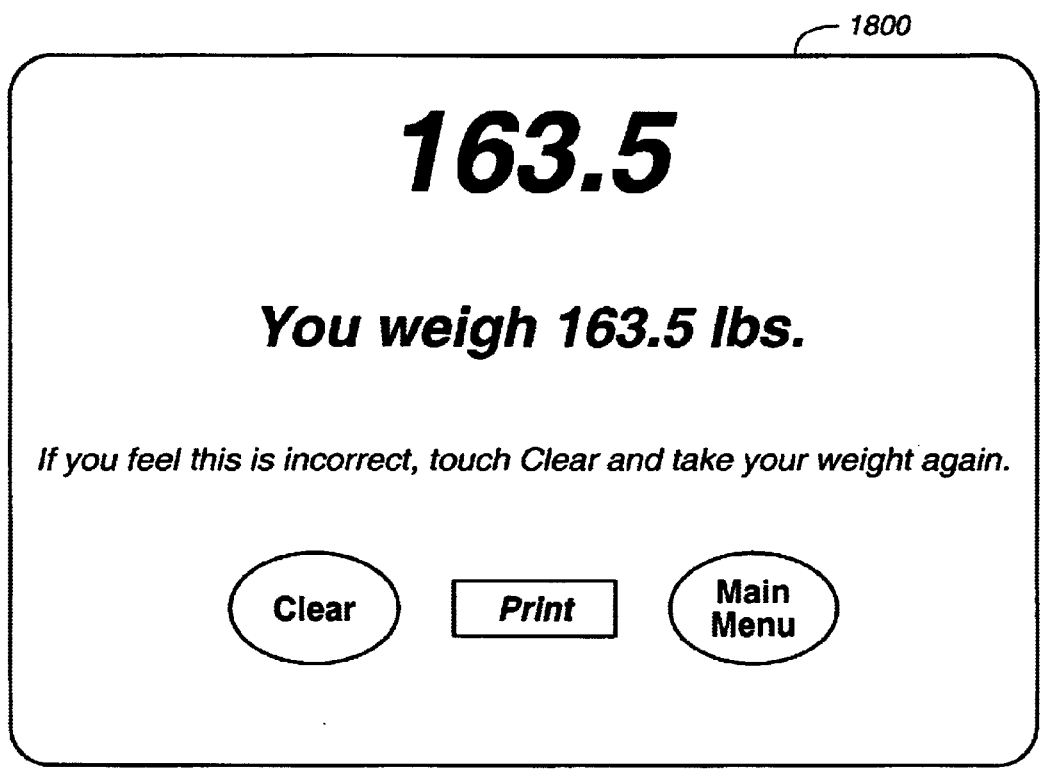
FIG._18

HEALTH CARE INFORMATION SYSTEM

BACKGROUND OF THE INVENTION

The field of medicine has long employed health care screening to diagnose and tract patients' health. An annual physical examination is a well-known part of patient medical care.

Hospitals, health clinics, and pharmacies, in addition to an active role is supplying medical supplies and pharmaceuticals, have actively promoted various health care screenings and wellness programs. Programs are sometimes offered with the help of other health care providers or coordinated on a national basis with groups such as the American Lung Association, the American Diabetes Association and the American Podiatric Medical Association.

Health care screening devices in hospitals, physician's offices, businesses, and the like, in combination with the growing number of home diagnostic kits that are available have increased the efficiencies in health care delivery. Chain drug store operators have increasingly encouraged individual testing by making available in-store diagnostic testing devices. For example, a pharmacist who fills a high-blood pressure medicine for a customer may encourage the customer to regularly check blood pressure. The customer may use a blood pressure measurement and screening device in the drug store.

To increase attention to the health care screening category, many medical and health produce retailers offer medical tests and screening for consumers visiting their stores. Most commonly, the retailers check cholesterol levels and blood pressure, although many other tests are available. In addition to supplying a valuable customer service, in-store testing effectively educates consumers about various health problems that can be better managed by a regimen that includes monitoring. Typically consumers are unaware of the technological advances that have made health care screenings feasible in the clinical, retail, and home settings. Pharmacies and drug retailers have generally found that point out that the availability of screening test devices in the stores increases traffic and cultivates customer loyalty.

The offer of in-store testing commonly is highly popular among customers and greatly boosts the number of people visiting the store. In-store testing is valuable for positioning stores as health and wellness centers as well as retailers of health care products. In-store testing increases sales since a consumer who learns of a health problem through screening in the store has some likelihood of purchasing a home test kit to monitor the problem. For example, a customer who discovers a problem of high blood pressure through an in-store test is a likely candidate to purchase a home test kit.

In-store health care screening expands the pharmacist's role in patient care through education. Test device manufacturers have advanced the design and functionality of products to simplify usage and improve accuracy. The challenge for further improvements in health care screening is to educate consumers about the need for medical tests, and demonstrate that many tests are effectively performed by publicly available devices or at home.

A present concern is that health screening is performed on an insufficient segment of the population to efficiently prevent or treat ailments. Other concerns are that health screening is too costly, limited in scope, and time-consuming both for individual patients and health care providers. Despite these deficiencies, a strong awareness exists of a need and desire for improved health screening procedures and equipment. Health care providers, insurance companies, and employers that ultimately pay for health care have encouraged development and usage of improved, accurate yet economic health screening facilities both for treatment and prevention of health care problems.

Generally individual doctors and small groups of doctors have insufficient capital to maintain a complete health screening facility. Even if more health care providers were suitably equipped, typically only a small part of the population exploits health screening facilities due to time and cost considerations and apathy.

What are needed are health screening devices, facilities, and methods that can be placed in locations that are convenient to health care customers. Suitable locations include retail outlets such as pharmacies or drug stores where customers already make health care purposes, but also include medical offices or hospitals, convalescence and elderly care homes, work places such as offices or factory sites, college dormitories, and the like. What are further needed are health screening devices, facilities, and methods that are convenient, efficient, low in cost, and professionally accurate in screening health care data.

SUMMARY

In accordance with one aspect of the present invention, a health kiosk provides blood pressure testing, a health and fitness evaluation, and a medication encyclopedia. The health kiosk typically interfaces to a computer or server, such as a pharmacy computer or a remote server which compares pharmaceuticals selected by a user to information in the medication encyclopedia to determine compatibility for prescription medications and over-the-counter medications. In some systems, the kiosk also supplies one item or more of an extended health information, a weight scale constructed into the seat of the kiosk, a directory of health care service and product providers, an a directory of community health, support, and service groups.

The health services and information system delivers services in areas ranging from patient education, medical research, dispensing of counseling and health information, and disease state management to database centralization of pharmacist-owners' credentials. The health services and information system includes a network web site that supplies consumers with information about such topics as nutrition and fitness, women's and men's health, diabetes, asthma, HIV and other health conditions. Consumers also use the web site to locate a nearby pharmacy.

Health care screenings are integral to delivery of services since screenings clearly set forth a customer's goals and needs.

The health services and information system supports third-party prescription plans and uses a managed care network to contract for third-party business on behalf of its network of stores. The managed care network allows a retailer to compete on an equal basis with chains for third-party contracts. Otherwise, most independent retailers would be locked out of the third party contracts.

Along with increased buying power, franchisees have access to support services including a nationally coordinated marketing program with health care screenings. Although, only basic blood pressure testing is described, the health services and information system can additionally support more sophisticated evaluations including vision tests, and evaluations of cholesterol levels and body fat. For example, other tests that can be performed include colorectal cancer tests, blood glucose screenings, glaucoma tests, screening for foot fungus infections, and others.

BRIEF DESCRIPTION OF THE DRAWINGS

The features of the described embodiments believed to be novel are specifically set forth in the appended claims. However, embodiments of the invention relating to both structure and method of operation, may best be understood by referring to the following description and accompanying drawings.

FIG. 1 is a schematic block diagram illustrating a suitable network for interconnecting one or more health information kiosks and a health information server.

FIG. 2 is a pictorial diagram illustrating a suitable health information kiosk for usage in interfacing to a health services and information system.

FIG. 3 is a pictorial diagram illustrating another view of the suitable health information kiosk with improved visualization of a blood pressure cuff.

FIG. 4 is a pictorial computer screen display illustrating a main menu screen that is initially displayed when health services and information system software is activated.

FIGS. 5A and 5B depict pictorial computer screen displays including a blood pressure testing start screen and a blood pressure testing end screen.

FIGS. 6A, 6B, and 6C are graphic displays showing pressure waveforms depicting examples of data that are analyzed to perform blood pressure measurements.

FIGS. 7A and 7B are pictorial computer screen displays associated with a health risk appraisal function, including a questionnaire form for setting user parameters and a health care appraisal result screen.

FIGS. 8A and 8B are pictorial computer screen displays associated with a medication encyclopedia display function.

FIGS. 9A and 9B are pictorial computer screen displays that illustrate a health information display function.

FIGS. 10A, 10B, 10C, and 10D are pictorial computer screen displays that illustrate a local community information display function.

FIGS. 11A and 11B are pictorial computer screen displays that illustrate a "Shopping Mall" business access display function.

FIGS. 12A and 12B are pictorial computer screen displays showing a blood pressure history access screen to allow protected access to a user's blood pressure history information.

FIGS. 13A, 13B, and 13C depict several examples of schematic graphs that show collective user health data.

FIG. 14 is an example of a table showing a compilation of acquired samples of health care data that can be generated by the health services and information system.

FIG. 15 is an example of a test printout that can be produced by the health services and information system.

FIG. 16 is a schematic screen display showing an entry screen for user identifying information for use in saving and accessing secured patient information.

FIG. 17 is a schematic screen display that illustrates a registration form for a web site.

FIG. 18 is a schematic screen display illustrating a weight measurement result screen.

DESCRIPTION OF THE PREFERRED EMBODIMENT(S)

Referring to FIG. 1, a schematic block diagram illustrates a suitable network 102 for interconnecting one or more health information kiosks 110 and a health information server 104. Typically, an individual health information kiosk 110 includes a processor 106 or controller with a storage 108 or memory that maintains a local archive of user information that stores a relatively small number of relatively recent test results, measurements, and possibly other information. The processor 106 executes a logic (not shown), typically a computer program that includes health services and information system software 120, that is stored as software, firmware, control logic or other executable forms as are known by one of ordinary skill in the art. In an illustrative health services and information system 100, the health information kiosk 110 employs additional computing power by adding a digital signal processor (DSP) 112 that operates in conjunction with the processor 106 to perform computation-intensive operations such as various health test operations.

The local archive includes tracking of health reading including blood pressure, heart rate and weight. Individual users also have an individual personal health site on the health information server 104. The health information server 104 is generally used to store a long-term archive of user results, measurements, and information received from the individual health information kiosks 110. In one example, the local health information kiosk 110 stores information from many users and all information that is generated on the health information kiosk 110 is automatically loaded, for example on a daily basis, to the central health information server 104. The results are sent to the health information server 104 for long-term storage and archiving. The information for the individual users are stored on corresponding personal health sites that are assigned to the particular individual users so that accurate and current information are available for all of the individual users.

In the illustrative example, the individual users determine the degree and level of health care information to be acquired and stored on the site. The individual user assigns a privilege level to allow the user's physician or pharmacist to enter information to the site with a desired level of security. The physician or pharmacist having the privilege granted by the individual user gains entry to the user site upon entry of a physician or pharmacist license or registration number granted by a federal, state, or local licensing authority. Entry of the licensing or registration number enforces user security and privacy concerns, preventing fraudulent change to the user database. Using the secured access to the user's site, the physician can be allowed to download health care information to the user site. Information is not changed on the site so the physician's level of security insures accuracy of the downloaded information. The physician's security specification permits the physician to transmit secured prescription orders and records to the individual health care site.

The health services and information system 100 benefits the individual users by permitting secured accessibility of health care information and prescription needs anywhere in the world through usage of the internet. The health services and information system 100 supplies accurate and current individual health care information that is accessible in a crisis or emergency situation.

In one example, the health information server 104 includes a layered security program for protecting user data from privacy violations. In an example of a layered security program, a user's personal health site can have a sixteen digit security card for entry into the health information kiosk 110 and an individual personal identification (PID) number to access the user's personal health site on the health information server 104. The level of security is equivalent to the security of an ATM machine in which the only person having access is the user since the user establishes the PID number.

The health information kiosks 110 are generally accessible to the public. For example, pharmacies or drug stores are suitable facilities for supplying floor space for a health information kiosk 110. Other suitable facilities include other retail outlets, health care providers such as physician offices, clinics, hospitals, and the like. The facilities housing a health information kiosk 110 typically have an agreement with the kiosk supplier to supply information, services, and products. The health information kiosk 110 executes various functions such as health testing and health evaluation. In some systems, the health information kiosk 110 supports operations including health testing and measurement, health and fitness evaluation, and various health care information sources. Various health tests may be supported. Common health tests include blood pressure testing, heart rate testing, and the like. For example, some systems may support various noninvasive blood analyses using pulse oximetry data acquisition. Measurements may include simple or complex measurements. One common measurement is a weight measurement that is supplied using a seat scale that is installed into the seat of the health information kiosk 110. Health care information sources may include a medication encyclopedia, a vitamin and supplement encyclopedia, an electronic health care library, health care provider directories, and the like.

The health information kiosk 110 interfaces to a server such as a store computer system or to a centralized server that services a wide geographical area. For example, the health information kiosk 110 may interface to a local pharmacy or drug store computer. The health information kiosk 110 may alternatively interface to a main frame health information server 104 that services a large area such as a country or region of the world. The health information kiosk 110 in combination with the health information server 104 typically includes a highly comprehensive pharmacy library covering prescription medications and over-the-counter remedies.

The individual health information kiosks 110 commonly include display software that displays a selected idle presentation, an attract screen with still-frame or dynamic graphics, or plays video clips that promote a selected party such as the sponsoring store or medical service providers.

Software programs in the individual health information kiosks 110 is updated by downloading, for example via internet access, or media transfer such as removable disk loading.

The health information server 104 commonly supports Internet sites for user access of health information, storage of personal history information, and to shop for products that are not available local to the health information kiosk 110.

Referring to FIGS. 2 and 3, a pictorial diagram shows a suitable health information kiosk 110 for usage in interfacing to a health services and information system 100. The health information kiosk 110 includes a test interface 212 and a display 216. The display 216 can be configured to form a touch-screen keyboard for some data input operations. Some examples of the health information kiosk 110 can include a measurement interface 222 such as a weighing scale. The test interface 212 and display 216 are connected to a processor or controller (not shown) that executes diagnostic test operations using data acquired using the test interface 212. In an illustrative example, the test interface 212 is a blood pressure cuff 213 for acquiring blood pressure measurements. A microphone 211 is attached to the blood pressure cuff 213 to measure a sound or audio signal. The display 216 in a configuration as a user interface or keyboard is used to acquire patient data and other information from the user. The processor includes communication interfaces for communicating with the test interface 212, the display 216, and a remote terminal so that the health information kiosk 110 can be connected into a communication network (not shown). In some systems, the health services and information system 100 includes a telephone handset (not shown) that a user may employ to receive information from the health services and information system 100 in privacy or for usage in telephone communication. Some versions of the health information kiosk 110 optionally include a printer 220 for printing test results, information materials, advertisements, coupons, and the like.

The illustrative test interface 212 is a blood pressure cuff 213 with one or more pressure transducers (not shown) for acquiring blood pressure waveforms from the user. The pressure transducer has an electrical connection to the processor via the communication interface so that pressure waveform data is supplied to the processor. The processor executes a computerized blood pressure detection algorithm to produce highly accurate measurements of systolic and diastolic blood pressure, and mean blood pressure. The processor also analyzes the blood pressure waveforms to detect heart rate information.

The processor executes software programs including data analysis routines that produce highly accurate blood pressure and heart rate measurements. The health services and information system 100 acquires other health care information from the patient and from various health care databases via network communication linkages to generate a full health appraisal. The health services and information system 100 includes local storage and the network communication link to external storage resources to allow a user to access pertinent health care information. For example, the health services and information system 100 permits the user to access a full medication encyclopedia that lists pharmaceutical medications that are currently available on the market. A health care provider directory is accessible via the network interconnection, either on the kiosk or by an Internet connection, to enable the user to find area physicians, specialists, clinics, hospitals, health maintenance organizations (HMOs), and the like.

One example of a suitable display 216 is a high-resolution Active Matrix color touchscreen display. The display 216 is used to present menus and controls, as well as to present information including test results, measurements, health information such as seasonal health information. A text display shows text in one or more of various selected languages. Many other displays of various sizes, specifications, and utilizing various technologies are also suitable.

One example of a suitable test interface 212 is a blood pressure cuff 213 including a nylon washable exterior cuff with a seamless inner natural latex bladder that is inflated using a pneumatic power system. A suitable cuff size is 30×12.5 cm. The cuff can be constructed of medical grade silicone tubing that is non-reactive, and thus allergy-free, to body tissue. Cuff pressure is regulated by pressure monitors (not shown) that are inherently stable and are calibrated to function accurately with cuff pressure variations of less than +/−1% over a full operating range of systolic maximum pressure 250 mm-Hg and minimum pressure 80 mm-Hg, and diastolic maximum pressure 130 mm-Hg and minimum pressure 38 mm-Hg, a differentiation of 8 points between systolic and diastolic pressure, and a heart rate from 38 to 200 bpm. The monitors use automatic zero pressure variations to prevent accuracy from being affected by altitude level or other changes in atmospheric pressure, temperature, and humidity. The exemplary test interface 212 also detects sound signals for usage with Korotkoff sound detection. Both pressure signals and sound signals are converted to digital form and transmitted to the processor to perform blood pressure measurements using both oscillometric and auscultatory analysis. The pressure and sound signals can be processed to determine heart rate measurement using a beat-to-beat averaging method. In some examples, tests are activated using a touch screen in which a virtual green start button initiates a test procedure by inflating the cuff positioned about the patient's arm. Touching the display screen halts the test and returns the pneumatic cuff to the open position. Various other specifications, materials, and technologies or combinations of technologies that are known by those having ordinary skill in the art are also suitable.

An illustrative measurement interface 222 is a weighing scale formed into a moveable seat 224 that is attached to the health information kiosk 110. The seat scale has accuracy within one pound. In some systems, the seat 224 of the health information kiosk 110 is moveable so that the test interface 212 and display 216 are wheel-chair accessible and easily used by the disabled without assistance.

Referring to FIG. 4, a pictorial computer screen display illustrates a main menu screen 402 that is initially presented when health services and information system software 120 is activated. The health services and information system software 120 is a program employing a graphical user interface to receive information from a user and to display selected display screens to the user. The graphical user interface of the health services and information system software 120 is generally a touch screen display in which various touch buttons are actuated when the user touches a defined region on the display screen. In one example, the main menu screen 402 has several touch buttons including a blood pressure test button 410, a health risk appraisal button 412, a medication encyclopedia button 414, a health information selection button 416, a community directory button 418, a special coupons access button 420. The main menu screen 402 further includes a vitamins and minerals selection button 422, a blood pressure history button 424, a weighing function request button 426, and a personal health site button 428. The main menu screen 402 permits the user to touch a selection to begin multifaceted access to the health services and information system database. The main menu screen 402 facilitates user access to information concerning the specific user's health, the local community, the business or businesses sponsoring the health information kiosk 110 executing the health services and information system software 120.

When the user actuates the blood pressure test button 410, the health services and information system software 120 displays a blood pressure testing start screen 500, shown in FIG. 5A, that instructs the user in performing a self-test of blood pressure. The blood pressure testing start screen 500 includes a graphic 502 that instructs the user to place an arm in the blood pressure cuff test interface 212 in an appropriate position. The blood pressure testing start screen 500 also has soft buttons including an illustration button 504 for displaying additional educational and instructional material regarding the blood pressure test procedure, a start button 506 that initiates operation of the test interface 212 to begin acquiring data, and a main menu button 508 that allows the user to return to the main menu screen 402.

The user places the left arm in the cuff as is shown on the display 216, touches a virtual start button on the display screen and the health services and information system 100 controls the test interface 212 to perform a blood pressure measurement in conjunction with computation operations executed by the processor 106 and, in some systems, the DSP 112. When the test is completed, the user touches a virtual touch print button to receive a printout of blood pressure results.

Pressing the start button 506 actuates the test interface 212 to begin the blood pressure testing, typically by inflating the blood pressure cuff 213, then gradually deflating the cuff while acquiring pressure and sound readings from the cuff. The sound and pressure measurements acquired by the test interface 212 are sent to processors including a digital signal processor (not shown) and a central processor (not shown) which process the measurements to determine blood pressure using one or more techniques. A first technique is a conventional sound (auscultatory) method. A second technique is a conventional pressure (oscillometric) method. A third technique calculates blood pressure using a combination of sound and pressure measurements. In some systems, blood pressure samples are determined using all three of the auscultatory, oscillometric, and combination techniques. A complete blood pressure waveform is acquired for a plurality of heart cycles and stored in memory for analysis, allowing a determination of both systolic and diastolic blood pressure after cuff pressure is deflated. In an illustrative system, the digital signal processor is capable of executing thirty-five million operations per second, to permit analysis of approximately 6500 samples in a single blood pressure test. In some systems, the heart rate is determined using a beat-to-beat averaging technique.

Referring to FIGS. 6A, 6B, and 6C, graphic displays of pressure waveforms are depicted which show examples of data that is analyzed to perform blood pressure measurements. FIG. 6A shows a Bell Curve of an actual blood pressure wave. FIG. 6B shows a magnified section of the blood pressure waveform. FIG. 6C displays a pressure waveform showing systolic and diastolic pressures.

When the blood pressure test is complete, the health services and information system software 120 displays a blood pressure testing end screen 520, shown in FIG. 5B, that displays results of the blood pressure test. The blood pressure testing end screen 520 includes a graphic 522 showing results of the blood pressure test including systolic pressure, diastolic pressure, and heart rate. The blood pressure results display rates the measured systolic and diastolic pressures in relation to desirable and unhealthy rates. The blood pressure testing end screen 520 has soft buttons including a store results button 524 for storing the patient's results in the patient's individual database, a health care appraisal button 526 which, like the health risk appraisal button 412 of the main menu screen 402, generates a health care appraisal screen. The blood pressure testing end screen 520 also has a main menu button 508 that allows the user to return to the main menu screen 402. The blood pressure testing end screen 520 has a print button that the user can actuate to generate a printout of the results for user record-keeping. In some systems an icon (not shown) may be supplied that allows a user to store history information to a personal secured database.

When the user actuates the health care appraisal button 526 on the blood pressure testing end screen 520 or the health risk appraisal button 412 on the main menu screen 402, the health services and information system software 120 generates and displays a health risk appraisal screen.

The pictorial computer screen displays associated with a health risk appraisal function, include a health care appraisal questionnaire form 700 for setting user parameters and a health care appraisal result screen 720, respectively shown in FIGS. 7A and 7B. The health services and information system software 120 first-displays the health care appraisal questionnaire form 700 filled with any previously available information. Fields in which data has not been entered request updating. The user may update filled fields by actuating a display bar showing a value in the field. In the illustrative system, the health care appraisal questionnaire form 700 displays the user's age 702, height 704, weight 706, gender 708, frame size 710, exercise habits 712, and smoking habits 714. Additional fields may be added to the health care appraisal questionnaire form 700 or a subsequent screen for setting additional conditions. The health care appraisal questionnaire form 700 also includes a continue button 716 for proceeding to additional questionnaire forms or for proceeding to the health care appraisal result screen 720.

The health care appraisal result screen 720 shown in FIG. 7B, displays results of the health risk appraisal including systolic pressure, diastolic pressure, heart rate, and appraisal ratings. The appraisal function is typically executed by the processor and combines blood pressure results, heart rate results, and answers to health-related questions to determine a health risk category for the user. The appraisal ratings include an appraisal score, a health rating, and the health risk rating.

User information including test results, measurement results, analysis, and personal information, if authorized by the user, can be entered into a customer database for usage by sponsors of the health information kiosk 110. The sponsors to attract user patronage of the kiosk and the sponsor of the kiosk may support a user rewards sign-up program.

The health care appraisal result screen 720 has a main menu button 730 that allows the user to return to the main menu screen 402, and has a print button which the user can actuate to generate a print-out of the results for user recordkeeping.

The health risk appraisal operation is based on data made available by the U.S. government in combination with the user blood pressure results. The user answers questions that are presented on the display 216. The health services and information system 100 determines a health risk appraisal and presents the appraisal results on the display screen. The user can actuate a virtual print button 732 on the display screen to print the results on the printer 220.

Referring to FIGS. 8A and 8B, several pictorial computer screen displays exemplify a medication encyclopedia display function. When the user is accessing the main menu screen 402 and actuates the medication encyclopedia button 414, the health services and information system software 120 displays a medication encyclopedia index screen 810, shown in FIG. 8A. In one example, the health services and information system 100 includes an encyclopedia of over 7500 over-the-counter and prescription medications. The encyclopedia specifies directions for using the medications, side effects, proper and improper usage, and other pertinent information. The medication encyclopedia index screen 810 includes a plurality of touch buttons in the form and arrangement of a virtual keyboard to allow the user to enter the first letters of a particular medication. In one example, when the user enters the first three letters of a medication, the health services and information system 100 displays the selected medication.

The medication information is supplied, for example, from the United States Pharmacopoeia leaflet patient version that is maintained as the information is regularly updated in government documents.

FIG. 8B depicts a medication entry screen 812, illustratively showing the description of an azatadine oral medication. The medication entry screen 812 includes several touch buttons for accessing additional information relating to the medication. A first button (WHAT) 814 is highlighted to signify that the display describes the medication. A second button (TELL) 816 describes usage for the medication. A third button (TAKE) 818 relates common dosages or dosages for the particular user, as determined by information from health care providers of the user or from user information in the database of the health services and information system 100. A fourth touch button (WARNING) 820 describes warnings regarding usage of the medication. A fifth touch button (SIDE EFFECTS) 822 informs the user of any known side effects of the medication. A sixth touch button (View Another Drug) 824 is used to return to the medication database to select additional medications that are commonly used for the same purposes as the accessed medication. A seventh touch button (DRUG INTERACTION) 826 is accessed to determine whether the medication taken in combination with any of the user's current medications will cause adverse reactions. An EXIT touch button 828 allows the user to return to the main menu screen 402.

When the user actuates the seventh touch button (DRUG INTERACTION) 826, a number keyboard is displayed to permit the user to enter a PIN number that protects the users private information database. The user first selects an over-the-counter product that is considered for usage and actuates the seventh touch button (DRUG INTERACTION) 826 from the medication encyclopedia. The user enters a personal identification number (PIN). The health services and information system software 120, typically executing on the processor, checks the pharmacy database and generates a response of either: (1) Interaction, Please see the Pharmacist, or (2) No Interaction—Use Allowed. After the search is completed, information is made accessible to the local pharmacist. The pharmacist collects a file of customers and interactions that are checked in subsequent references. A warning screen may be displayed.

Referring to FIGS. 9A and 9B, pictorial computer screen displays exemplify a health information display function. When the user is accessing the main menu screen 402 and actuates the health information selection button 416, the health services and information system software 120 displays a health information menu screen 910, shown in FIG. 9A. The health information menu screen 910 allows the user to link to various information sites relating to health care. Typically accessed entries are viewed and printed by the user, if desired. Many sites include color graphics and full motion video. The accessible selections can include standard entries or can be customized for a particular location of the health information kiosk 110. The illustrative health information menu screen 910 includes touch buttons to access disease information 914, information relating to the human body 916, exercise and fitness information 912, food facts 918, and medical facts 920. FIG. 9B depicts a disease screen 930 that can be displayed when user actuates the touch button for the disease information 912. The disease screen 930 includes touch buttons that the user can actuate to receive information relating to a particular disease or affliction.

The health information is displayed in several formats including text, graphics, full motion video, and on-line information optioned via Internet. For sensitive information, the user can lift the telephone handset (not shown) to listen to the topics in privacy.

Referring to FIGS. 10A, 10B, 10C, and 10D, pictorial computer screen displays illustrate a local community information display function. The community display generates a directory of local health care providers or medical facilities such as physicians, hospitals, emergency centers, crisis centers, and the like for display to a user. In addition to local health care providers and medical facilities, the health services and information system 100 also may generate entries that are regional, national, or international in scope, generally for providers of services that are more wide-ranging in scope. The community display also stores and displays information relating to schools, colleges, churches, and other public or service facilities.

When the user is accessing the main menu screen 402 and actuates the community directory button 418, the health services and information system software 120 displays a community services menu screen 1010, shown in FIG. 10A. The community services menu screen 1010 allows the user to link to various information sites relating to health care. Typically accessed entries are viewed and printed by the user, if desired. Many sites include color graphics and full motion video. The accessible selections can include standard entries or can be customized for a particular location of the health information kiosk 110. The illustrative community services menu screen 1010 includes touch buttons to access a physician directory 1012, a school directory 1014, a hospital directory 1016, a civic group's directory 1018, and a support groups directory 1020.

When the user actuates the support groups directory touch button 1020, the health services and information system software 120 displays a support groups menu 1030 that presents touch buttons for accessing directories of particular types of support groups. FIG. 10B depicts an example of a support groups menu screen 1030 that is displayed when user actuates a touch button for alcohol and drug abuse programs from the support groups menu screen 1030. The support groups menu screen 1030 includes touch buttons that the user can actuate to receive information relating to various treatment programs for treating a particular disease or affliction. In the illustrative system, one of the touch buttons on the support groups menu screen 1030 is an alcohol and drug abuse touch button 1032.

When the user actuates the alcohol and drug abuse touch button 1032, the health services and information system software 120 presents an alcohol and drug abuse service provider directory screen 1034, an example of which is shown in FIG. 10C. Entries in the alcohol and drug abuse service provider directory screen 1034 show the name, address, and telephone number of a listed alcohol and drug abuse service provider. The alcohol and drug abuse service provider directory screen 1034 has a cursor for pointing to a particular entry, an "up" button and a "down" button for scrolling through the list, and a "select" button for selecting a particular entry that is designated by the cursor.

When the user selects an entry, the health services and information system software 120 displays a screen showing additional information relating to the selected group. FIG. 10D shows a group screen for an alcoholics anonymous support group.

Using the community information display function, the user can obtain local and wide ranging information in a list format. Alternatively, if the health services and information system 100 includes the telephone handset (not shown), the user can use telephone communication via the telephone handset to connect directly to the community service organization of interest.

The community directory supplies a listing of local services and information that give the user finger-touch access to communicate with local physicians, hospitals, or support groups directly from the kiosk. Although the community information screen is described as including local information, this description is made primarily to indicate that information is customized for particular local communities. The community information commonly also includes groups, individuals, or organizations that are national or international in scope.

The community listing directory typically includes a full listing for each entry. The health services and information system 100 also supports more extension coverage of a particular entry. For example, a health care provider, group, or other entity may arrange for one or more information pages or an expanded video presentation on the display 216.

In some systems, a local bulletin board is supported and displayed on the health information kiosk 110 to supply information to employees of the organization supporting the kiosk. The bulletin board may be accessed via a selection on the community groups function or may be accessed in other ways.

Referring to FIGS. 11A and 11B, pictorial computer screen displays illustrate a special coupons access display function. When the user is accessing the main menu screen 402 and actuates the "Shopping Mall" business access button 420, the health services and information system software 120 displays a "Shopping Mall" business access menu screen 1100, shown in FIG. 11A. The "Shopping Mall" business access menu screen 1100 allows the user to access various advertisements, special offers, and coupons. Typically, accessed advertisements, offers, and coupons are viewed and printed by the user, if desired. The accessible selections can include standard entries or can be customized for a particular location and to support selected advertisers or clients associated with the health information kiosk 110. The illustrative "Shopping Mall" business access menu screen 1100 includes touch buttons to access pharmacy items 1102, groceries 1104, household items 1106, and mail order specials 1108. FIG. 11B depicts a grocery coupon screen 1110 that can be displayed when user actuates the touch button for the groceries 1104. The grocery coupon screen 1110 includes touch buttons that the user can actuate to receive printed grocery coupons, advertisements, and special offers. The coupons and informational materials are printed on the printer 220 when requested by the user.

Coupons can be printed from the health information kiosk 110, permitting point-of-purchase advertising and usage of seasonal specials. A mail-order program effectively expands the floor-space of a store using e-commerce by offering hundreds or thousands of additional products or services that a customer can order directly from the health information kiosk 110. The user can order the products or services directly from the health information kiosk 110 and arrange for purchased items to be made available for delivery at the kiosk location or delivered to the user. The "Shopping Mall" business access display function permits advertising using full motion commercials and coupons at a fraction of the cost of other media sources. The health services and information system 100 also supports online ordering for supported clients.

The health services and information system software 120 generates similar screens for accessing informational and ordering materials for purchases of vitamin and mineral supplements via a vitamins and minerals selection button 422. Information on vitamins, herbs, and minerals is available at a touch of the display screen. The information includes various remedies, studies, and documented interactions of concurrent remedies.

When the user actuates the blood pressure history button 424, the health services and information system software 120 displays a blood pressure history access screen 1200, shown in FIG. 12A, that allows protected access to the users blood pressure history information. The blood pressure history is stored as a sequence of time and date entries in a memory accessed and written by the processor within the health information kiosk 110. Entries are identified with a particular user and protected against access of others by usage of a PIN number or ID card. Upon identification of a user, the user can retrieve records from previous tests.

The blood pressure history access screen 1200 includes a numerical touch button pad that permits the user to enter an access number such as a social security number, a password, a PIN number, or the like. A system that utilizes personal identification numbers (PIN), the PIN number may be assigned according to a workplace (corporate) account, a store account at which the user is a customer, or a customer account assigned directly to the user.

In the illustrative health services and information system software 120, the user enters a Personal Identification Number (PIN) and/or inserts an access card and enters a PIN number to access the blood pressure history data. Also in the illustrative system, local memory of the health information kiosk 110 stores the most recent ten results. The user may select any desired result or group of results, including statistics that are derived from the results.

Blood pressure test results for the patient are displayed in FIG. 12B.

The health services and information system 100 collects and stores data for a plurality of users and generates overall average and trend information from the collective data, while maintaining the privacy of individual users. Various parties may use the collective data to supply inventory information, marketing studies, business planning, and the like. For example, parties using the collective data may include the store or facility in which the health information kiosk 110 is located, suppliers of medications and supplements, health care providers, insurers, and the like. Referring to FIGS. 13A, 13B, and 13C, several schematic graphs are depicted which show collective user health data. FIG. 13A shows a graph of health risk appraisal scores and data, according to gender, FIG. 13B shows a graph of health risk appraisal value according to smoking habits. FIG. 13C shows a graph of systolic and diastolic blood pressure. The illustrative graphs exemplify only a few of a myriad of possible statistical displays that may be displayed, as is known by those having ordinary skill in the art.

The health services and information system 100 stores and categorizes data from a user according to identification number. Stored data can be accessed for usage by commonly available spreadsheet software programs for review or presentation. Data may be stored according to identification number, data and time, or other arrangement.

Referring to FIG. 14, an example of a table show a compilation of acquired samples of health care data that can be generated by the health services and information system 100. The table is a compilation of the sequential transactions executed by the health services and information system 100 over a real time interval.

Referring to FIG. 15, an example of a test printout 1500 shows data that can be produced by the health services and information system 100 for access by a user. The kiosk produces a personal waveform printout with a blood pressure result printout 1502 when the user actuates the print button on the blood pressure testing end screen 520 to show the blood pressure result. A health risk appraisal result printout 1504 is generated by the health services and information system 100 when the user actuates the print button from the health care appraisal result screen 720. A blood pressure history result printout 1506 is produced when the user actuates the print button from the blood pressure history access screen 1200.

The user can actuate the Personal Health Site button 428 on the main menu screen 402 shown in FIG. 4 to store and access a secure personal health history. The user enters identifying information on a touch-screen display 1600, shown in FIG. 16, that is displayed following actuation of the Personal Health Site button 428. PIN numbers or other security measures secure patient information and prevent unauthorized access to confidential information.

In some systems, the user can be automatically connected to a proprietary web site after registration with the site. FIG. 17 is a schematic screen display that illustrates a registration form for a web site.

The user can actuate the weighing function request button 426 on the main menu screen 402, shown in FIG. 4, to activate the weight scale formed into the seat of the kiosk. The user reads the result from a weight measurement result screen 1800 shown in FIG. 18.

While the invention has been described with reference to various embodiments, it will be understood that these embodiments are illustrative and that the scope of the invention is not limited to them. Many variations, modifications, additions and improvements of the embodiments described are possible. For example, those skilled in the art will readily implement the steps necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims.

In the claims, unless otherwise indicated the article "a" is to refer to "one or more than one".

What is claimed is:

1. A kiosk-based system for accessing health-related services and information, comprising:

a controller;

local storage coupled to the controller;

a kiosk comprising a user-interactive display, the user-interactive display being coupled to the controller, and providing access to a health services and information system;

a communications interface coupled to the controller; and health test interface coupled to the controller;

the controller being capable of communicating with a remote server that comprises a remote storage via the communications interface, and comprising:

logic for controlling the health test interface to performing measurements on a user to acquire user health test measurement data;

logic for processing the user health test measurement data to generate a user health test result;

logic for controlling storage of the user health test result in the local storage in a user local storage element allocated for the user; and logic for controlling storage of the health test result in the remote storage in a user remote storage element allocated for the user.

2. The system of claim 1, wherein the controller further comprises logic for controlling display of the user health test result and a health test result history via the user-interactive display.

3. The system of claim 1, wherein the controller further comprises logic for appraising health risk and controlling display of the user health test result and a health risk appraisal via the user-interactive display.

4. The system of claim 1, wherein the health test interface composes blood pressure measuring equipment.

5. The system of claim 1, farther comprising:
a measurement interface coupled to the controller;
wherein the control further comprises:
logic for controlling the measurement interface to measure a diagnostic parameter and provide a user measurement result; and
logic for controlling storage of the user measurement result in the user local storage element.

6. The system of claim 1, further comprising:
a measurement interface coupled to the controller for measuring the weight of the user;
wherein the controller further comprises:
logic for controlling the measurement interface to measure weight and provide a user weight measurement result; and
logic for controlling storage of the user weight measurement result in the user local storage element.

7. The system of claim 1, wherein the controller further comprises:
logic for executing an interactive information transfer session via the user-interactive display to obtain user information for storage in, and retrieval from, at least one of the local storage and the remote storage.

8. The system of claim 1, further comprising:
logic, at least partly executable via the controller, that secures data in at least one of the user local storage element and the user remote storage element against unauthorized access.

9. The system of claim 1, further comprising:
logic, at least partly executable via the controller, that automatically transfers data in the local storage to the remote storage.

10. The system of claim 1, further comprising:
logic, at least partly executable via the controller and at least partly executable via the remote server, providing access to the health services and information system.

11. The system of claim 1, further comprising:
logic, at least partly executable via the server and at least partly executable via the remote server, providing access to health-related directory information.

12. The system of claim 1, further comprising:
logic, at least partly executable via the server and at least partly executable via the remote server, providing access to a health-related service or product for order, transfer or purchase via electronic commerce.

13. The system of claim 1, further comprising:
logic, at least partly executable via the server and at least partly executable via the remote server, providing access to health-related information concerning compatibility of at least two treatments selected from a group consisting of a health-related medication, a health-related remedy, a health-related supplement, and any combination thereof.

14. The system of claim 1, wherein the user-interactive display is housed by the kiosk.

15. The system of claim 1, wherein the controller, the local storage, and the communications interface are housed by the kiosk.

16. The system of claim 1, wherein the health services and information system provides access to health-related information is selected from a group consisting of nutrition information, medication information, remedy information, vitamin-, mineral-, or herbal-supplemnent information, fitness information, sex-specific information, condition-specific information, educational information, research information, counseling information, health information, disease state management information, health-related information from a network information source, provider credential information, provider directory information, community-specific information, community directory information, business information, and any combination thereof.

17. The system of claim 1, the user-interactive display providing access to information for ordering, transferring or purchasing a health-related product or service.

18. A kiosk-based system for accessing health-related services and information, comprising:
a controller;
local storage coupled to the controller;
a kiosk comprising a user-interactive display, the user-interactive display being coupled to the controller and providing access to a health services and information system;
a communications interface coupled to the controller; and
a health test interface coupled to the controller;
the controller being capable of communicating with a remote server, having a remote storage, via the communications interface, and comprising:
logic for controlling the health test interface to perform measurements on a user to acquire user health test measurement data;
logic for processing the user health test measurement data to generate a user health test result;
logic for controlling storage of the user health test result in the local storage in a user local storage element allocated for the user; and
logic for controlling storage of the health test result in the remote storage in a user remote storage clement allocated for the user; and
logic, at least partly executable on the controller and at least partly executable on the remote server, providing access to health-related information via the interactive display.

19. The system of claim 18, wherein the logic providing access to health-related information provides access to health-related information from a network information source.

20. A kiosk-based system for accessing health-related services and information, comprising;
a server;
a server storage coupled to the server, the server being capable of storing at least one of a health test result and a health measurement for users in user storage elements, each user storage element being allocated to a user;
at least one kiosk, the kiosk comprising:
a controller;
a user-interactive display coupled to the controller, the user-interactive display providing access to a health services and information system; and
diagnostic equipment coupled to the controller;
the controller being capable of appraising user health risk from at least one of diagnostic test data acquired via the diagnostic equipment, user health-related information obtained via the user-interactive display, and user information stored in the user storage element; and
a communications interface coupled to the server, the server being capable of communicating with the kiosk via the communications interface to transfer at least one of the health test result and the health measurement from the kiosk to the server and to transfer at least the user health risk to the kiosk.

21. The system of claim 20, wherein the server is capable of providing to the kiosk a health test result history of users.

22. The system of claim 20, wherein the server is capable of providing to the kiosk a health risk appraisal of users.

23. The system of claim 20, wherein the diagnostic equipment is capable of measuring at least one of user blood pressure and user heart rate.

24. The system of claim 20, wherein the diagnostic equipment is capable of measuring user body weight.

25. The system of claim 20, wherein the server stores at least one of the health test result, the health measurement, and the user health-related information.

26. The system of claim 20, further comprising:
logic, at least partly executable via the server, that secures data in the user storage element against unauthorized access.

27. The system of claim 20, comprising:
logic, at least partly executable via the server and at least partly executable via the kiosk, providing access to health-related information via the interactive display.

28. The system of claim 20, further comprising:
logic, at least partly executable via the server and at least partly executable via the kiosk, providing access to health-related directory information.

29. The system of claim 20, further comprising:
logic, at least partly executable via the server and at least partly executable via the kiosk, providing access to a health-related service or product for order, transfer or purchase via electronic commerce.

30. The system of claim 20, further comprising:
logic, at least partly executable via the server and at least partly executable via the kiosk, providing access to health-related information concerning compatibility of at least two treatments selected from a group consisting of a health-related medication, a health-related remedy, a health-related supplement, and any combination thereof.

31. The system of claim 20, wherein the user-interactive display is housed by the kiosk.

32. The system of claim 20, wherein the controller and the communications interface are housed by the kiosk.

33. The system of claim 20, wherein the health services and information system provides access to health-related information is selected from a group consisting of nutrition information, medication information, remedy information, vitamin-, mineral-, or herbal-supplemnent information, fitness information, sex-specific information, condition-specific information, educational information, research information, counseling information, health information, disease state management information, health-related information from a network information source, provider credential information, provider directory information, community-specific information, community directory information, business information, and any combination thereof.

34. The system of claim 20, the user-interactive display providing access to health related information for ordering, or transferring or purchasing a health-related product or service.

35. A kiosk-based system for accessing health-related services and information, comprising: a server;
a server storage coupled to the server, the server being capable of storing a health test result and a health measurement for users in user storage elements, each user storage element being allocated to a user;
at least one kiosk, the kiosk comprising:
a controller;
a user-interactive display coupled to the controller and providing access to a health services and information system; and
diagnostic equipment coupled to the controller;
the controller being capable of appraising user health risk on the basis of diagnostic test data acquired via the diagnostic equipment, user health-related information obtained via the user-interactive display, and user information stored in the user storage element; and
a communications interface coupled to the server, the server being capable of communicating with the kiosk via the communications interface to transfer at least one of the health test result and the health measurement from the kiosk to the server and to provide health-related information.

36. The system of claim 35, wherein the server is capable of providing health-related information from a network information source to the kiosk.

37. A method of operating a kiosk-based system that comprises a kiosk, a controller and, coupled to the controller, a local storage, diagnostic equipment, a communications interface, and a user-interactive display of the kiosk the method comprising:
receiving information at the controller via the user-interactive display;
executing instructions at the controller comprising:
controlling the diagnostic equipment to perform a user health test measurement;
processing the health test measurement to produce a user health test result; controlling storage of the user health test result in the local storage in a user local storage element allocated for the user; and
communicating with a remote server that comprises a remote storage via the communications interface;
controlling storage of the user health test result in the remote storage in a user remote storage element allocated for the user; and
providing access to a health services and information system via the user-interactive display.

38. The method of claim 37, wherein executing instructions at the controller further comprises:
providing the user health test result and a health test result history via the user-interactive display.

39. The method of claim 37, wherein executing instructions at the controller further comprises:
appraising health risk based on at least one of the user health test result and information obtained via the user-interactive display; and
providing the user health test result and a health risk appraisal via the user-interactive display.

40. The method of claim 37, wherein the user health test measurement comprises at least one of a blood pressure measurement and a heart rate measurement.

41. The method of claim 37, wherein the system further comprises a measurement interface, and executing instructions at the controller further comprises:
controlling the measurement interface to measure a diagnostic parameter and provide a user measurement result; and
controlling storage of the user measurement result in the user local storage element.

42. The method of claim 37, wherein the system further comprises a measurement interface, and executing instructions at the controller further comprises:
controlling the measurement interface to measure weight and provide a user weight measurement result; and controlling storage of the user weight measurement result in the user local storage element.

43. The method of claim 37, wherein executing instructions at the controller further comprises:

controlling execution of an interactive information transfer session via the user-interactive display to obtain user information for storage in, and retrieval from, at least one of the local storage and the remote storage.

44. The method of claim 43, further comprising:

appraising health risk based on at least one of the user health test result and the user information obtained via the user-interactive display.

45. The method of claim 37, further comprising:

securing data in at least one of the user local storage element and the user remote storage element against unauthorized access.

46. The method of claim 37, further comprising: automatically transferring data in the local storage to the remote storage.

47. The method of claim 37, wherein providing access to a health services and information system comprises providing access to health-related service directory information.

48. The method of claim 37, wherein providing access to health services and information system comprises providing access to a health-related service or product for order, transfer or purchase via electronic commerce.

49. The method of claim 37, wherein providing access to a health services and information system comprises providing access to health-related information concerning compatibility of at least two treatments selected from a group consisting of a health-related medication, a health-related remedy, a health-related supplement, and any combination thereof.

50. The method of 37, wherein the user-interactive display is housed by a the kiosk and providing access to a health services and information system comprises providing access to health-related information via the user-interactive display of the kiosk.

51. The method of claim 37, wherein providing access to a health services and information system comprises providing access to health-related information is selected from a group consisting of nutrition information, medication information, remedy information, vitamin-, mineral-, or herbal-supplement information, fitness information, sex-specific information, condition-specific information, educational information, research information, counseling information, health information, disease state management information, health-related information from a network information source, provider credential information, provider directory information, community-specific information, community directory information, business information, and any combination thereof.

52. The method of claim 37, wherein providing access to a health services and information system comprises providing access to information for ordering, transferring or purchasing a health-related product or service.

53. A method of operating a kiosk-based system comprising a kiosk a controller and, coupled to the controller, a local storage, a health test interface, a communications interface, and a user-interactive display of the kiosk, the method comprising:

receiving information at the controller via the user-interactive display;

acquiring a user health test measurement from the health test interface;

executing instructions at the controller comprising:
processing the user health test measurement to produce a user health test result;
controlling storage of the user health test result in the local storage in a user local storage element allocated for the user;
communicating with a remote server that comprises a remote storage via the communications interface;
controlling storage of the user health test result in the remote storage in a user remote storage element allocated for the user;
controlling the measurement interface to measure weight and provide a user weight measurement result; and
controlling storage of the user weight measurement result in the local storage in the user local storage element; and providing access to a health services and information system via the user-interactive display.

54. The method of claim 53, wherein the user-interactive display is housed by the kiosk and providing access to a health services and information system comprises providing access to health-related information via the user-interactive display of the kiosk.

55. A method of operating a kiosk-based system comprising a kiosk, a controller and, coupled to the controller, a local storage, blood pressure measurement equipment, a communications interface for communicating with a remote server, and a user-interactive display of the kiosks the method comprising:

receiving information at the controller via the user-interactive display;

acquiring a first measurement of user blood pressure via the blood pressure measurement equipment;

storing the first measurement of user blood pressure at the remote server;

acquiring at least one subsequent measurement of user blood pressure via the blood pressure measurement equipment;

storing the subsequent measurement of user blood pressure at the remote server;

generating a user blood pressure history by retrieving the first and the subsequent measurement of user blood pressure from the remote server; and providing access to a health services and information system via the user-interactive display.

56. The method of claim 55, wherein the user-interactive display is housed by a the kiosk and providing access to a health services and information system comprises providing access to health-related information via the user-interactive display of the kiosk.

57. The method of any of claim and 55, wherein providing access to a health services and information system comprises providing access to health-related information selected from a group consisting of nutrition information, medication information, remedy information, vitamin-, mineral-, or herbal-supplement information, fitness information, sex-specific information, condition-specific information, educational information, research information, counseling information, health information, disease state management information, health-related information from a network information source, provider credential information, provider directory information, community-specific information, community directory information, business information, and any combination thereof.

* * * * *

(12) EX PARTE REEXAMINATION CERTIFICATE (8555th)
United States Patent
Bluth et al.

(10) Number: US 6,692,436 C1
(45) Certificate Issued: Sep. 20, 2011

(54) HEALTH CARE INFORMATION SYSTEM

(75) Inventors: Charles Bluth, Incline Village, NV (US); James Bluth, Verdi, NV (US)

(73) Assignee: Computerized Screening Inc., Reno, NV (US)

Reexamination Request:
No. 90/010,779, Dec. 17, 2009

Reexamination Certificate for:
| Patent No.: | 6,692,436 |
| Issued: | Feb. 17, 2004 |
| Appl. No.: | 09/549,451 |
| Filed: | Apr. 14, 2000 |

(51) Int. Cl.
*A61B 5/022* (2006.01)
*A61B 5/00* (2006.01)

(52) U.S. Cl. .................. 600/300; 128/904; 128/920; 600/301; 702/19

(58) Field of Classification Search .................. 600/300
See application file for complete search history.

(56) References Cited

U.S. PATENT DOCUMENTS

| 5,867,821 A | 2/1999 | Ballantyne |
| 5,987,519 A | 11/1999 | Peifer et al. |
| 6,336,136 B1 | 1/2002 | Harris |
| 6,602,469 B1 | 8/2003 | Maus |
| 7,287,031 B1 | 10/2007 | Karpf et al. |

FOREIGN PATENT DOCUMENTS

EP 0329306 8/1989

OTHER PUBLICATIONS

Warner, Dave, "The Webification of Medicine: Interventional Informatics Through the WWW." San Diego, California, Jan. 1997.
Warner, Dave, "Distributed Medical Intelligence: A Systems Approach for Developing an Integrative Healthcare Information Distribution Infrastructure." San Diego, California, Jan. 1996.
Holfelder, A Networked Multimedia Retrieval Management System for Distributed Kiosk Applications, 1994 (IEEE).
CardioAnalysis Systems, Owner's Manual Assembly Instructions, Apr. 1992.

*Primary Examiner* — Samuel Rimell

(57) ABSTRACT

A health kiosk provides blood pressure testing, a health and fitness evaluation, and a medication encyclopedia. The health kiosk typically interfaces to a computer or server, such as a pharmacy computer or a remote server which compares pharmaceuticals selected by a user to information in the medication encyclopedia to determine compatibility for prescription medications and over-the-counter medications. In some systems, the kiosk also supplies one item or more of an extended health information, a weight scale constructed into the seat of the kiosk, a directory of health care service and produce providers, an a directory of community health, support, and service groups.

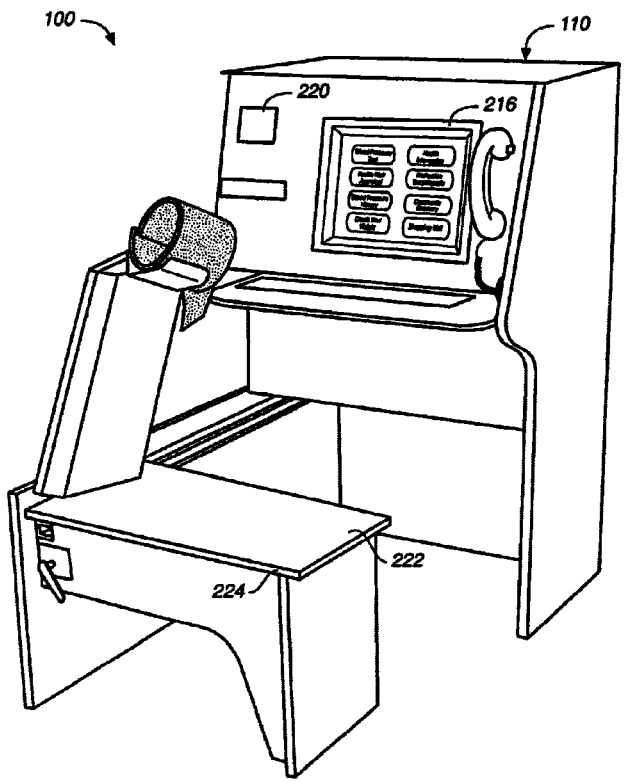

US 6,692,436 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-3, 6-10, 14, 15, 17, 37-49 and 52 is confirmed.

Claims 4-5, 11-13, 16, 18, 20-24, 33, 35-36, 50-51, 53 and 55-57 are determined to be patentable as amended.

Claims 19, 25-32, 34 and 54, dependent on an amended claim, are determined to be patentable.

New claims 58-65 are added and determined to be patentable.

4. The system of claim 1, wherein the health test interface [composes] *comprises* blood pressure measuring equipment.
5. The system of claim 1, [farther] *further* comprising:
  a measurement interface coupled to the controller;
  wherein the [control] *controller* further comprises:
    logic for controlling the measurement interface to measure a diagnostic parameter and provide a user measurement result; and
    logic for controlling storage of the user measurement result in the user local storage element.
11. The system of claim 1, further comprising:
  logic, at least partly executable via the [server] *controller* and at least partly executable via the remote server, providing access to health-related directory information.
12. The system of claim 1, further comprising:
  logic, at least partly executable via the [server] *controller* and at least partly executable via the remote server, providing access to a health-related service or product for order, transfer or purchase via electronic commerce.
13. The system of claim 1, further comprising:
  logic, at least partly executable via the [server] *controller* and at least partly executable via the remote server, providing access to health-related information concerning compatibility of at least two treatments selected from a group consisting of a health-related medication, a health-related remedy, a health-related supplement, and any combination thereof.
16. The system of claim 1, wherein the health services and information system provides access to health-related information [is] selected from a group consisting of nutrition information, medication information, remedy information, vitamin-, mineral-, or [herbal-supplemnent] *herbal-supplement* information, fitness information, sex-specific information, condition-specific information, educational information, research information, counseling information, health information, disease state management information, health-related information from a network information source, provider credential information, provider directory information, community-specific information, community directory information, business information, and any combination thereof.
18. A kiosk-based system for accessing health-related services and information, comprising:
  a controller;
  local storage coupled to the controller;
  a kiosk comprising a user-interactive display, the user-interactive display being coupled to the controller and providing access to a health services and information system;
  a communications interface coupled to the controller; and
  a health test interface coupled to the controller;
  the controller being [capable of communicating] *configured to communicate* with a remote server, having a remote storage, via the communications interface, and comprising:
    logic for controlling the health test interface to perform measurements on a user to acquire user health test measurement data;
    logic for processing the user health test measurement data to generate a user health test result;
    logic for controlling storage of the user health test result in the local storage in a user local storage element allocated for the user; and
    logic for controlling storage of the health test result in the remote storage in a user remote storage element allocated for the user; and
    logic, at least partly executable on the controller and at least partly executable on the remote server, providing access to health-related information via the interactive display.
20. A kiosk-based system for accessing health-related services and information, comprising:
  a server;
  a server storage coupled to the server, the server being [capable of storing] *configured to store* at least one of a health test result and a health measurement for users in user storage elements, each user storage element being allocated to a user;
  at least one kiosk, the kiosk comprising:
    a controller;
    a user-interactive display coupled to the controller, the user-interactive display providing access to a health services and information system; and
    diagnostic equipment coupled to the controller;
  the controller being [capable of appraising] *configured to appraise* user health risk from at least one of diagnostic test data acquired via the diagnostic equipment, user health-related information obtained via the user-interactive display, and user information stored in the user storage element; and
  a communications interface coupled to the server, the server being [capable of communicating] *configured to communicate* with the kiosk via the communications interface to transfer at least one of the health test result and the health measurement from the kiosk to the server and to transfer at least the user health risk to the kiosk.
21. The system of claim 20, wherein the server is [capable of providing] *configured to provide* to the kiosk a health test result history of users.
22. The system of claim 20, wherein the server is [capable of providing] *configured to provide* to the kiosk a health risk appraisal of users.
23. The system of claim 20, wherein the diagnostic equipment is [capable of measuring] *configured to measure* at least one of user blood pressure and user heart rate.

24. The system of claim 20, wherein the diagnostic equipment is [capable of measuring] *configured to measure* user body weight.

33. The system of claim 20, wherein the health services and information system provides access to health-related information is selected from a group consisting of nutrition information, medication information, remedy information, vitamin-, mineral-, or [herbal-supplemnent] *herbal-supplement* information, fitness information, sex-specific information, condition-specific information, educational information, research information, counseling information, health information, disease state management information, health-related information from a network information source, provider credential information, provider directoyr information, community-specific information, community directory information, businesss information, and any combination thereof.

35. A kiosk-based system for accessing health-related services and information, comprising:
   a server;
   a server storage coupled to the server, the server being [capable of storing] *configured to store* a health test result and a measurement for users in user storage elements, each user storage element being allocated to a user;
   at least one kiosk, the kiosk comprising:
      a controller;
      a user-interactive display coupled to the controller and providing access to a health services and information system; and
      diagnostic equipment coupled to the controller;
   the controller being [capable of appraising] *configured to appraise* user health risk on the basis of diagnostic test data acquired via the diagnostic equipment, user health-related information obtained via the user-interactive display, and user information stored in the user storage element; and
   a communications interface coupled to the server, ther server being [capable of communicating] *configured to communicate* with the kiosk via the communications interface to transfer at least one of the health test result and the health measurement from the kiosk to the server and to provide health-related information.

36. The system of claim 35, wherein the server is [capable of providing] *configured to provide* health-related information from a network information source to the kiosk.

50. The method of 37, wherein the user-interactive display is housed by [a] *the* kiosk and providing access to a health services and information system comprises providing access to health-related information via the user-interactive display of the kiosk.

51. The method of claim 37, wherein providing access to a health services and information system comprises providing access to health-related information [is] selected from a group consisting of nutrition information, medication information, remedy information, vitamin-, mineral-, or herbal supplement information, fitness information, sex-specific information, condition-specific information, educational information, research information, counseling information, health information, disease state management information, health-related information from a network information source, provider credential information, provider directory information, community-specific information, community directory information, business information, and any combination thereof.

53. A method of operating a kiosk-based system comprising a kiosk, a controller and, coupled to the controller, a local storage, a health test interface, a communications interface, and a user-interactive display of the kiosk, the method comprising:
   receiving information at the controller via the user-interactive display;
   acquiring a user health test measurement from the health test interface;
   executing instructions at the controller comprising:
      processing the user health test measurement to produce a user health test result;
      controlling storage of the user health test result in the local storage in a user local storage element allocated for the user;
      communicating with a remote server that comprises a remote storage via the communications interface;
      controlling storage of the user health test result in the remote storage in a user remote storage element allocated for the user;
      controlling the measurement interface to measure weight and provide a user weight measurement result; and
      controlling storage of the user weight measurement result in the local storage in the user local storage element; and
   providing access to a health services and information system via the user-interactive display.

55. A method of operating a kiosk-based system comprising a kiosk, a controller and, coupled to the controller, a local storage, blood pressure measurement equipment, a communications interface for communicating with a remote server, and a user-interactive display of the [kiosks] *kiosk,* the method comprising:
   receiving information at the controller via the user-interactive display;
   acquiring a first measurement of user blood pressure via the blood pressure measurement equipment;
   storing the first measurement of user blood pressure at the remote server;
   acquiring at least one subsequent measurement of user blood pressure via the blood pressure measurement equipment;
   storing the subsequent measurement of user blood pressure at the remote server;
   generating a user blood pressure history by retrieving the first and the subsequent measurement of user blood pressure from the remote server; and
   providing access to a health services and information system via the user-interactive display.

56. The method of claim 55, wherein the user-interactive display is housed by [a] *the* kiosk and providing access to a health services and information system comprises providing access to health-related information via the user-interactive display of the kiosk.

57. The method [of any] of claim [and] 55, wherein providing access to a health services and information system comprises providing access to health-related information selected from a group consisting of nutrition information, medication information, remedy information, vitamin-, mineral-, or herbal-supplement information, fitness information, sex-specific information, condition-specific information, educational information, research information, counseling information, health information, disease state management information, health-related information from a network information source, provider credential information, provider directory information, community-specific information, community directory information, business information, and any combination thereof.

58. A kiosk-based system for accessing health-related services and information comprising:
   at least one kiosk comprising:
      a controller;
      local storage coupled to the controller;
      a user-interactive display coupled to the controller, and providing access to a health services and information system;
      a communications interface coupled to the controller; and
      a health test interface coupled to the controller;
   the controller being configured to communicate automatically via the communications interface with a remote server that comprises a remote storage, and comprising:
      logic for controlling the health test interface to perform measurements on a user to acquire user health test measurement data;
      logic for processing the user health test measurement data to generate a user health test result;
      logic for controlling storage of the user health test result in the local storage in a user local storage element allocated for the user;
      logic for controlling storage of the health test result in the remote storage in a user remote storage element allocated for the user; and
      logic for receiving from the remote server health-related services and information.

59. The system of claim 58, wherein, in the at least one kiosk, the controller further comprises:
   logic for collecting, storing, and processing data for a plurality of users to generate average or trend information from the plurality of users.

60. The system of claim 59, wherein the logic for collecting, storing, and processing data maintains privacy of individual users.

61. The system of claim 59, wherein the user-interactive display comprises a touch-screen display.

62. The system of claim 1, wherein the user-interactive display comprises a touch-screen display.

63. The system of claim 18, wherein the user-interactive display comprises a touch-screen display.

64. The system of claim 20, wherein the user-interactive display comprises a touch-screen display.

65. The system of claim 35, wherein the user-interactive display comprises a touch-screen display.

* * * * *